US012751600B2

(12) United States Patent
Chiba

(10) Patent No.: US 12,751,600 B2

(45) Date of Patent: Oct. 6, 2026

(54) INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Haruto Chiba, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 276 days.

(21) Appl. No.: 18/614,770

(22) Filed: Mar. 25, 2024

(65) Prior Publication Data

US 2024/0324848 A1 Oct. 3, 2024

(30) Foreign Application Priority Data

Mar. 28, 2023 (JP) ................................ 2023-052392

(51) Int. Cl.
*A61B 1/00* (2006.01)
*A61B 1/267* (2006.01)

(52) U.S. Cl.
CPC ...... *A61B 1/00009* (2013.01); *A61B 1/00045* (2013.01); *A61B 1/2676* (2013.01)

(58) Field of Classification Search
None
See application file for complete search history.

(56) References Cited

U.S. PATENT DOCUMENTS 11,398,048 B2 * 7/2022 Lopez Mendez ....... G06T 7/593
2011/0135172 A1 6/2011 Kitamura
2015/0057498 A1 2/2015 Akimoto et al.
2020/0219272 A1 * 7/2020 Pizer ...................... G06V 20/46
2022/0071711 A1 * 3/2022 Kyperountas ........... G06T 17/00
2022/0257978 A1 * 8/2022 Kamen ................ A61N 5/1039
(Continued)

FOREIGN PATENT DOCUMENTS

JP 2010220742 10/2010
JP 5718537 5/2015

OTHER PUBLICATIONS

Jake Sganga et al., "OffsetNet: Deep Learning for Localization in the Lung using Rendered Images", Proceedings of IEEE International Conference on Robotics and Automation (ICRA), May 2019, pp. 1-7.

(Continued)

*Primary Examiner* — Nurun Flora
(74) *Attorney, Agent, or Firm* — JCIPRNET

(57) ABSTRACT

An information processing apparatus including at least one processor, wherein the processor is configured to: acquire an input image including a real image, which represents an interior wall of a tubular structure, or a virtual image, which represents, in a pseudo manner, the interior wall as viewed from a virtual viewpoint; use a transformation model to transform the input image into a transformed image having an image style that is not included in the input image; acquire an input depth image, which represents a distance for each pixel from a viewpoint of the input image to the interior wall, and a transformed depth image, which represents a distance for each pixel from a viewpoint of the transformed image to the interior wall; and train the transformation model by using a loss function including a degree of similarity between the input depth image and the transformed depth image.

11 Claims, 25 Drawing Sheets

(56) References Cited

U.S. PATENT DOCUMENTS

2023/0410334 A1* 12/2023 Nishimura ................ G06T 7/50
2024/0324849 A1* 10/2024 Chiba ................ A61B 1/00045

OTHER PUBLICATIONS

Mehmet Turan et al., "Deep EndoVO: A Recurrent Convolutional Neural Network (RCNN) based Visual Odometry Approach for Endoscopic Capsule Robots", Proceedings of IEEE Computer Vision and Pattern Recognition (CVPR), Sep. 2017, pp. 1-24.
Faisal Mahmood et al., "Unsupervised Reverse Domain Adaptation for Synthetic Medical Images via Adversarial Training", IEEE Transactions on Medical Imaging, vol. 37, Jun. 2018, pp. 1-10.
Mali Shen et al., "Context-Aware Depth and Pose Estimation for Bronchoscopic Navigation", IEEE Robotics and Automation Letters, vol. 4, Jan. 2019, pp. 1-8.

* cited by examiner

INFORMATION PROCESSING APPARATUS, INFORMATION PROCESSING METHOD, AND INFORMATION PROCESSING PROGRAM

CROSS-REFERENCE TO RELATED APPLICATIONS

This application claims priority from Japanese Application No. 2023-052392, filed on Mar. 28, 2023, the entire disclosure of which is incorporated herein by reference.

BACKGROUND

Technical Field

The present disclosure relates to an information processing apparatus, an information processing method, and an information processing program.

Related Art

In the related art, a tubular structure, such as a large intestine or a bronchus, of a patient is observed or treated by using an endoscope. An endoscopic image is an image in which a color and texture inside the tubular structure are clearly expressed by an imaging element, such as a charge coupled device (CCD), and represents the inside of the tubular structure as a two-dimensional image. Therefore, it is difficult to understand which position inside the tubular structure is represented by the endoscopic image. In particular, since the bronchus has a small diameter and a narrow visual field, it is difficult to reach a target position with a distal end of the endoscope.

Therefore, various methods have been proposed, which navigate a route to the target point in the tubular structure by using a virtual endoscopic image generated based on a three-dimensional image acquired by tomography using modalities, such as a computed tomography (CT) apparatus and a magnetic resonance imaging (MRI) apparatus. For example, JP5718537B proposes a method of acquiring route information indicating a route of a tubular structure based on a three-dimensional image, generating a large number of virtual endoscopic images along the route based on the three-dimensional image, and performing matching between the virtual endoscopic image and a real endoscopic image, to specify a distal end position of an endoscope.

In addition, for example, Jake Sganga, David Eng, Chauncey Graetzel, David B. Camarillo. "Offsetnet: Deep learning for localization in the lung using rendered images." In Proceedings of IEEE International Conference on Robotics and Automation (ICRA), pp. 5046-5052, 2019. proposes a method of identifying a real viewpoint, that is, a position of an endoscope by estimating a viewpoint difference between a real endoscopic image and a virtual endoscopic image by using a learning model. In the learning model in Jake Sganga, David Eng, Chauncey Graetzel, David B. Camarillo. "Offsetnet: Deep learning for localization in the lung using rendered images." In Proceedings of IEEE International Conference on Robotics and Automation (ICRA), pp. 5046-5052, 2019. is trained using, as training data, a combination of the real viewpoints obtained from the real endoscopic image and an electromagnetic sensor, a combination of the virtual endoscopic image and the viewpoint thereof, and the viewpoint difference thereof. In addition, it is also described that, in order to reinforce the training data, a combination of the viewpoints specified based on an image obtained by transforming the virtual endoscopic image into a real endoscopic image style and the three-dimensional image is used as the training data, instead of the combination of the real viewpoints obtained by the real endoscopic image and the electromagnetic sensor.

In addition, as another method of navigating the route to the target point in the tubular structure, for example, Mehmet Turan, Yasin Almalioglu, Helder Araujo, Ender Konukoglu, Metin Sitti. "Deep EndoVO: A recurrent convolutional neural network (RCNN) based visual odometry approach for endoscopic capsule robots." In Proceedings of IEEE Computer Vision and Pattern Recognition (CVPR), 2017. proposes a method of estimating a viewpoint difference between frames of a moving image acquired from an endoscope capsule, by using an estimated depth.

In addition, for example, Faisal Mahmood, Richard Chen, Nicholas J. Durr. "Unsupervised Reverse Domain Adaptation for Synthetic Medical Images via Adversarial Training." In Proceedings of IEEE Transactions on Medical Imaging (Volume: 37, Issue: 12), 2018. describes that a large intestine endoscopic image is transformed into a virtual endoscopic style image by using a generative adversarial network (GAN), and the depth is estimated based on the virtual endoscopic image. In Faisal Mahmood, Richard Chen, Nicholas J. Durr. "Unsupervised Reverse Domain Adaptation for Synthetic Medical Images via Adversarial Training." In Proceedings of IEEE Transactions on Medical Imaging (Volume: 37, Issue: 12), 2018., a constraint is applied so that an image change amount in a pixel unit is reduced before and after the transformation.

In addition, for example, in Mali Shen, Yun Gu, Ning Liu, Guang-Zhong Yang. "Context-Aware Depth and Pose Estimation for Bronchoscopic Navigation." In Proceedings of IEEE Robotics and Automation Letters (Volume: 4, Issue: 2), 2019. describes that a real bronchoscope image is transformed into a depth image by using a GAN, and a depth is estimated. In Mali Shen, Yun Gu, Ning Liu, Guang-Zhong Yang. "Context-Aware Depth and Pose Estimation for Bronchoscopic Navigation." In Proceedings of IEEE Robotics and Automation Letters (Volume: 4, Issue: 2), 2019., the transformed depth image is transformed into a bronchoscope image again, and a constraint is applied so that the bronchoscope image is matched with the original real bronchoscope image, thereby storing a bronchus structure in the image. In addition, Mali Shen, Yun Gu, Ning Liu, Guang-Zhong Yang. "Context-Aware Depth and Pose Estimation for Bronchoscopic Navigation." In Proceedings of IEEE Robotics and Automation Letters (Volume: 4, Issue: 2), 2019. describes that ground truth data of the depth image is automatically extracted from CT.

Meanwhile, the real endoscopic image may include noise that is not included in the virtual endoscopic image. For example, since the endoscope is inserted into the tubular structure, body fluids or the like may adhere to a lens of the endoscope distal end and the lens may be fogged. In addition, for example, an object that cannot be captured by tomography may appear in the real endoscopic image. In addition, for example, fine texture such as gloss and a blood vessel that is generated on an interior wall of the real tubular structure may be omitted in the virtual endoscopic image generated based on the three-dimensional image.

In a case in which noise is included in the real endoscopic image, the viewpoint difference between the real endoscopic image and the virtual endoscopic image cannot be estimated, and a real position of the endoscope cannot be specified. That is, there may be a case in which the route to the target point in the tubular structure cannot be accurately navigated.

SUMMARY

The present disclosure provides an information processing apparatus, an information processing method, and an information processing program capable of accurately estimating a viewpoint difference between a real image and a virtual image of an endoscope.

A first aspect of the present disclosure relates to an information processing apparatus comprising: at least one processor, in which the processor acquires an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image, uses a transformation model, which is trained to transform any one of the input real image or virtual image into an image style of the other of the input real image or virtual image, to transform the input image into a transformed image having an image style that is not included in the input image, acquires an input depth image, which represents a distance for each pixel from a viewpoint of the input image to the interior wall of the tubular structure, and a transformed depth image, which represents a distance for each pixel from a viewpoint of the transformed image to the interior wall of the tubular structure, and trains the transformation model by using a loss function including a degree of similarity between the input depth image and the transformed depth image.

In the first aspect, the transformation model may be obtained by a generative adversarial network that has been trained by using training data including a real image for training, which is captured by the endoscope inserted into the tubular structure of the subject and which represents the interior wall of the tubular structure, and a virtual image for training, which is generated based on a three-dimensional image of a subject that is the same as or different from the subject of the real image for training and which represents, in a pseudo manner, the interior wall of the tubular structure as viewed from the virtual viewpoint predetermined in the three-dimensional image.

In the first aspect, the input image may include the real image, the transformation model may be a learning model trained to receive input of the real image, transform the input real image into a virtual image style, and output the transformed real image, and the processor may transform the real image into a transformed image having the virtual image style by using the transformation model.

In the first aspect, the input image may include the virtual image, the transformation model may be a learning model trained to receive input of the virtual image, transform the input virtual image into a real image style, and output the transformed virtual image, and the processor may transform the virtual image into a transformed image having the real image style by using the transformation model.

In the first aspect, the processor may use a depth image generation model that has been trained in advance to receive input of an image, which represents the interior wall of the tubular structure, and output a depth image, which represents a distance for each pixel from the viewpoint of the input image to the interior wall of the tubular structure, to generate the input depth image based on the input image and the transformed depth image based on the transformed image.

In the first aspect, the depth image generation model may be a model that has been trained in advance through supervised learning using training data including a combination of a virtual image for training, which is generated based on the three-dimensional image of the subject and which represents, in a pseudo manner, the interior wall of the tubular structure as viewed from the virtual viewpoint predetermined in the three-dimensional image, and a depth image for training, which is generated based on distance information from the virtual viewpoint in the three-dimensional image to the interior wall of the tubular structure and which represents a distance for each pixel from the virtual viewpoint to the interior wall of the tubular structure.

In the first aspect, the depth image generation model may be a model that has been trained in advance through supervised learning using training data including a combination of an image obtained by transforming a virtual image for training, which is generated based on the three-dimensional image of the subject and which represents, in a pseudo manner, the interior wall of the tubular structure as viewed from the virtual viewpoint predetermined in the three-dimensional image, into a real image style by using a transformation model that has been trained in advance to receive input of the virtual image, transform the input virtual image into the real image style, and output the transformed virtual image, and a depth image for training, which is generated based on distance information from the virtual viewpoint in the three-dimensional image to the interior wall of the tubular structure and which represents a distance for each pixel from the virtual viewpoint to the interior wall of the tubular structure.

In the first aspect, the depth image generation model may be a model that has been trained through supervised learning using training data including a combination of a real image for training, which is captured by the endoscope inserted into the tubular structure of the subject and which represents the interior wall of the tubular structure, and a depth image for training, which is generated based on distance information from a viewpoint corresponding to a viewpoint at which the real image for training is captured, in the three-dimensional image of the subject, to the interior wall of the tubular structure and which represents a distance for each pixel from the viewpoint corresponding to the viewpoint at which the real image for training is captured to the interior wall of the tubular structure.

In the first aspect, the depth image generation model may be a model that has been trained in advance through supervised learning using training data including a combination of a real image for training, which is captured by the endoscope inserted into the tubular structure of the subject and which represents the interior wall of the tubular structure, and a depth image for training, which is generated based on an actual measurement value of a distance from a viewpoint at which the real image for training is captured to the interior wall of the tubular structure, the actual measurement value being obtained by a distance-measuring sensor mounted on the endoscope, and which represents a distance for each pixel from the viewpoint at which the real image for training is captured to the interior wall of the tubular structure.

A second aspect of the present disclosure relates to an information processing method including: acquiring an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image; using a transformation model, which is trained to transform any one of the input real image or virtual image into an image style of the other of the input real image or virtual image, to transform the input image into a transformed image having an image style that is not included in the input image; acquiring an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and training the transformation model by using a loss function including a degree of similarity between the input depth image and the transformed depth image.

A third aspect of the present disclosure relates to an information processing program for causing a computer to execute a process including: acquiring an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image; using a transformation model, which is trained to transform any one of the input real image or virtual image into an image style of the other of the input real image or virtual image, to transform the input image into a transformed image having an image style that is not included in the input image; acquiring an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and training the transformation model by using a loss function including a degree of similarity between the input depth image and the transformed depth image.

According to the aspects described above, the information processing apparatus, the information processing method, and the information processing program according to the present disclosure can accurately estimate the viewpoint difference between the real image and the virtual image of the endoscope.

DETAILED DESCRIPTION

Figure 1:
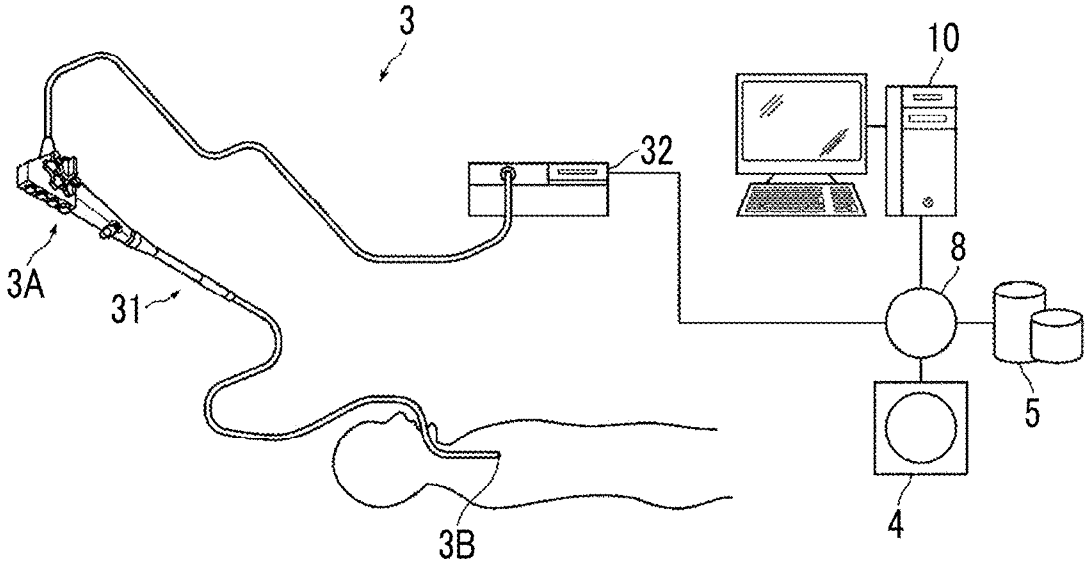
FIG. 1 is a diagram showing an example of a schematic configuration of an information processing system.

Hereinafter, description of an embodiment of the present disclosure will be made with reference to the accompanying drawings. FIG. 1 is a schematic configuration diagram of an information processing system to which an information processing apparatus 10 according to the present embodiment is applied. As shown in FIG. 1, in the information processing system, an endoscope apparatus 3, a three-dimensional image capturing apparatus 4, an image storage server 5, and the information processing apparatus 10 are connected to each other in a communicable state via a network 8.

The endoscope apparatus 3 comprises an endoscope 31 that images an inside of a tubular structure of a subject, a processor device 32 that generates an image of the inside of the tubular structure based on a signal obtained by the imaging, and the like. Examples of the tubular structure include a bronchus, a large intestine, and a small intestine.

In the endoscope 31, an insertion part to be inserted into the tubular structure of the subject is attached continuously with an operating part 3A. The endoscope 31 is connected to the processor device 32 via a universal cord that is attachably and detachably connected to the processor device 32. The operating part 3A includes various buttons for giving an instruction for an operation such that a distal end 3B of the insertion part is bent in an up-down direction and a left-right direction within a predetermined angle range, or operating a puncture needle attached to the distal end of the endoscope 31 to collect a tissue sample. The endoscope 31 is, for example, a bronchoscope, a large intestine endoscope, a small intestine endoscope, a laparoscope, and a thoracoscope.

In the present embodiment, the endoscope 31 is a flexible endoscope for the bronchus, and is inserted into the bronchus of the subject. Then, light guided by an optical fiber from a light source device (not shown) provided in the processor device 32 is applied from the distal end 3B of the insertion part of the endoscope 31, and the image of the inside of the bronchus of the subject is acquired by an imaging optical system of the endoscope 31. It should be noted that, in order to facilitate the description, the distal end 3B of the insertion part of the endoscope 31 will be referred to as an endoscope distal end 3B in the following description.

The processor device 32 transforms an imaging signal captured by the endoscope 31 into a digital image signal, and corrects an image quality by digital signal processing, such as white balance adjustment and shading correction, to generate a real image T0. That is, the real image TO is an image that is captured by the endoscope inserted into the tubular structure (bronchus) of the subject and represents the interior wall of the tubular structure (bronchus). The real image T0 is a color moving image displayed at a predetermined sampling rate, such as 30 fps, and one frame of the moving image is the real image T0. The real image T0 is sequentially transmitted to, for example, the image storage server 5 and the information processing apparatus 10.

The three-dimensional image capturing apparatus 4 is an apparatus that images an examination target part of the subject to generate a three-dimensional image representing the part, and is, specifically, a CT apparatus, an MRI apparatus, a positron emission tomography (PET) apparatus, an ultrasound diagnostic apparatus, or the like that captures an image by a method other than a method of inserting an endoscope 31 into a tubular structure to capture the tubular structure. The three-dimensional image generated by the three-dimensional image capturing apparatus 4 is transmitted to and stored in the image storage server 5. In the present embodiment, the three-dimensional image capturing apparatus 4 generates a three-dimensional image V0 obtained by imaging a chest including the bronchus. It should be noted that, in the present embodiment, the three-dimensional image capturing apparatus 4 is the CT apparatus, but the present disclosure is not limited to this.

The image storage server 5 is a computer that stores and manages various data, and comprises a large-capacity external storage device and software for database management. The image storage server 5 communicates with another device via the network 8, and transmits and receives image data and the like to and from the other device. Specifically, the image data, such as the real image T0 acquired by the endoscope apparatus 3, the three-dimensional image V0 generated by the three-dimensional image capturing apparatus 4, and a virtual image K0 generated by the information processing apparatus 10, are acquired via the network, are stored in a recording medium, such as a large-capacity external storage device, and are managed. It should be noted that the real image T0 is a moving image. Therefore, it is preferable that the real image T0 is transmitted to the information processing apparatus 10 without passing through the image storage server 5. It should be noted that a storage format of the image data or the communication between the devices via the network 8 is based on a protocol, such as digital imaging and communication in medicine (DICOM).

Meanwhile, the real image T0 of the endoscope is an image in which the color, texture, and the like of the inside of the tubular structure are clearly represented, but represents the inside of the tubular structure as a two-dimensional image. Therefore, it is difficult to understand which position inside the tubular structure is represented by the real image T0. In particular, since the bronchus has a small diameter and a narrow visual field, it is difficult to reach a target position with the endoscope distal end 3B.

Therefore, the information processing apparatus 10 according to the present embodiment supports enabling to understand which position inside the tubular structure is represented by the real image T0 based on the real image T0 obtained by the endoscope apparatus 3 and the three-dimensional image V0 obtained by the three-dimensional image capturing apparatus 4. Specifically, the information processing apparatus 10 performs viewpoint difference estimation processing of estimating a viewpoint difference ΔL between a virtual viewpoint that is virtually set in the three-dimensional image V0 and a viewpoint of the real image T0. Hereinafter, description of an example of the information processing apparatus 10 according to the present embodiment will be made.

Figure 2:
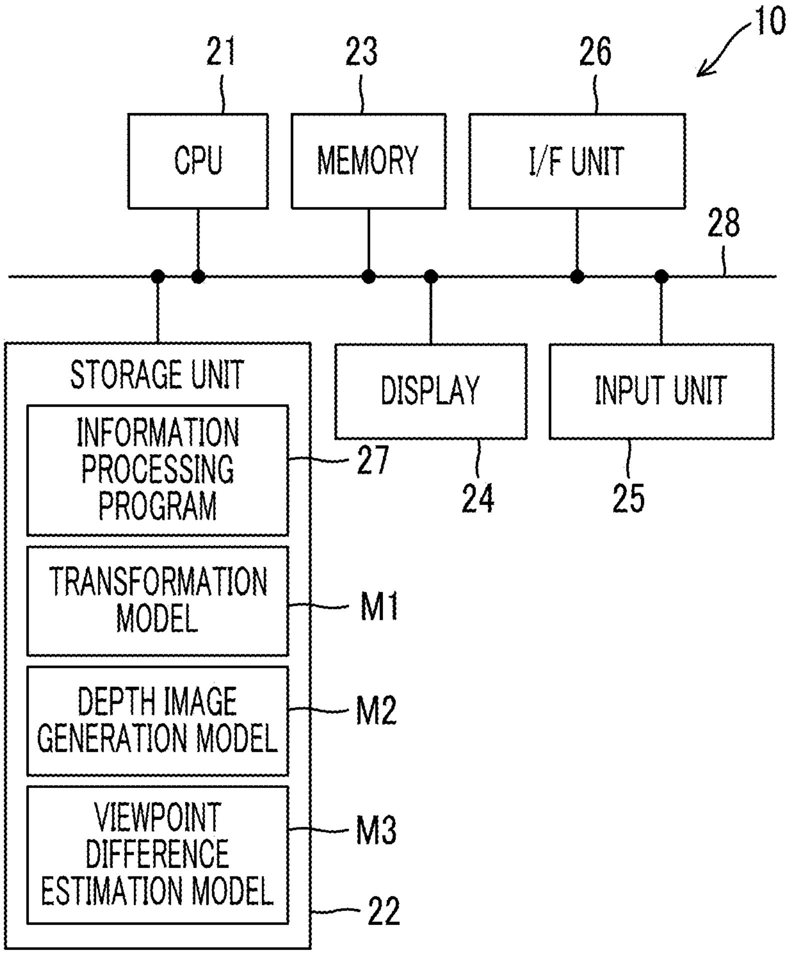
FIG. 2 is a block diagram showing an example of a hardware configuration of an information processing apparatus.

First, description of an example of a hardware configuration of the information processing apparatus 10 will be made with reference to FIG. 2. As shown in FIG. 2, the information processing apparatus 10 includes a central processing unit (CPU) 21, a non-volatile storage unit 22, and a memory 23 as a temporary storage area. Further, the information processing apparatus 10 includes a display 24, such as a liquid crystal display, an operation unit 25, such as a touch panel, a keyboard, and a mouse, and an interface (I/F) unit 26. The I/F unit 26 performs wired or wireless communication with the endoscope apparatus 3, the three-dimensional image capturing apparatus 4, the image storage server 5, other external apparatuses, and the like. The CPU 21, the storage unit 22, the memory 23, the display 24, the operation unit 25, and the I/F unit 26 are connected to each other via a bus 28, such as a system bus and a control bus, so that various types of information can be exchanged.

The storage unit 22 is realized by, for example, a storage medium, such as a hard disk drive (HDD), a solid state drive (SSD), and a flash memory. The storage unit 22 stores an information processing program 27 of the information processing apparatus 10. The CPU 21 reads out the information processing program 27 from the storage unit 22, deploys the read-out program into the memory 23, and executes the deployed information processing program 27. The CPU 21 is an example of a processor according to the present disclosure. The storage unit 22 stores a transformation model M1, a depth image generation model M2, and a viewpoint difference estimation model M3. As the information processing apparatus 10, for example, a personal computer, a server computer, a smartphone, a tablet terminal, a wearable terminal, or the like can be applied as appropriate.

Figure 3:
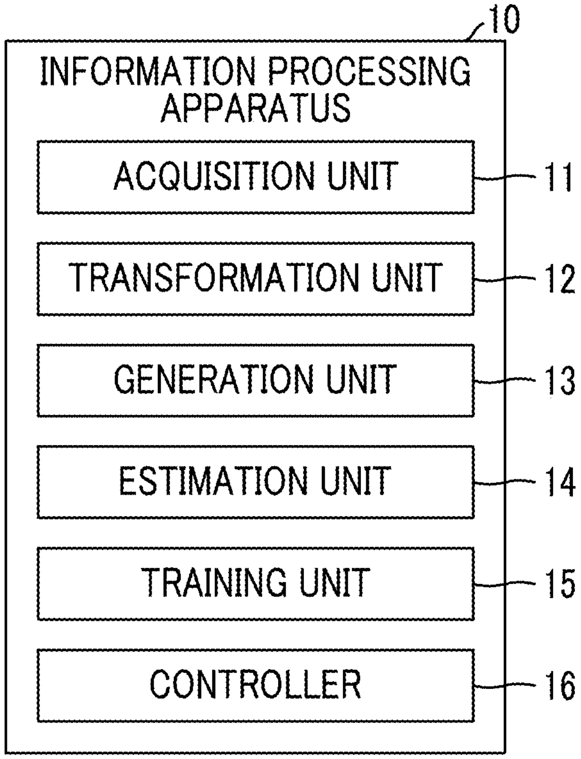
FIG. 3 is a block diagram showing an example of a functional configuration of the information processing apparatus.

Next, description of an example of a functional configuration of the information processing apparatus 10 will be made with reference to FIG. 3. As shown in FIG. 3, the information processing apparatus 10 includes an acquisition unit 11, a transformation unit 12, a generation unit 13, an estimation unit 14, a training unit 15, and a controller 16. As the CPU 21 executes the information processing program 27, the CPU 21 functions as the respective functional units of the acquisition unit 11, the transformation unit 12, the generation unit 13, the estimation unit 14, the training unit 15, and the controller 16.

The acquisition unit 11 acquires the real image T0 captured by the endoscope 31 disposed at a predetermined viewpoint position in the bronchus from the endoscope apparatus 3. It should be noted that the acquisition unit 11 may perform data compression processing on the real image T0 in order to reduce processing amounts in various types of processing to be described later. For example, the acquisition unit 11 may perform binarization based on a brightness value on the real image T0. In the following description, in a case in which the real image is simply referred to as the "real image T0", the real image T0 on which the data compression processing is performed is included.

In addition, the acquisition unit 11 acquires the three-dimensional image V0 of the subject captured by the three-dimensional image capturing apparatus 4. As described above, the three-dimensional image V0 is obtained, for example, by performing CT imaging on the chest including the bronchus, and consists of a plurality of tomographic images T1 to Tm (m is 2 or more) (see FIG. 6). It should be noted that, in a case in which the three-dimensional image V0 and the real image T0 are already stored in the storage unit 22, the image storage server 5, and the like, the acquisition unit 11 may acquire the three-dimensional image V0 and the real image T0 from the storage unit 22, the image storage server 5, and the like.

In addition, the acquisition unit 11 may acquire the virtual image K0 that is generated based on the three-dimensional image V0 and represents, in a pseudo manner, the interior wall of the tubular structure as viewed from a virtual viewpoint P10 predetermined in the three-dimensional image V0. Hereinafter, specific description of the acquisition method of the virtual image K0 based on the three-dimensional image V0 will be made.

Method Using Surface Rendering

Figure 4:
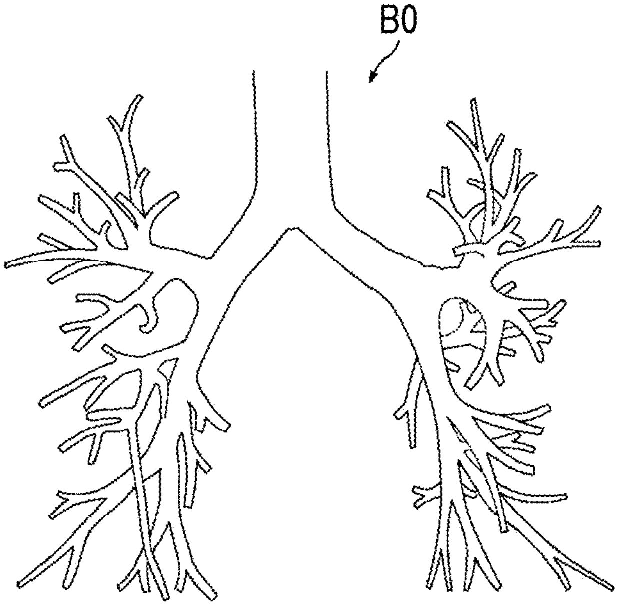
FIG. 4 is a diagram showing an example of a bronchus image.
Figure 5:
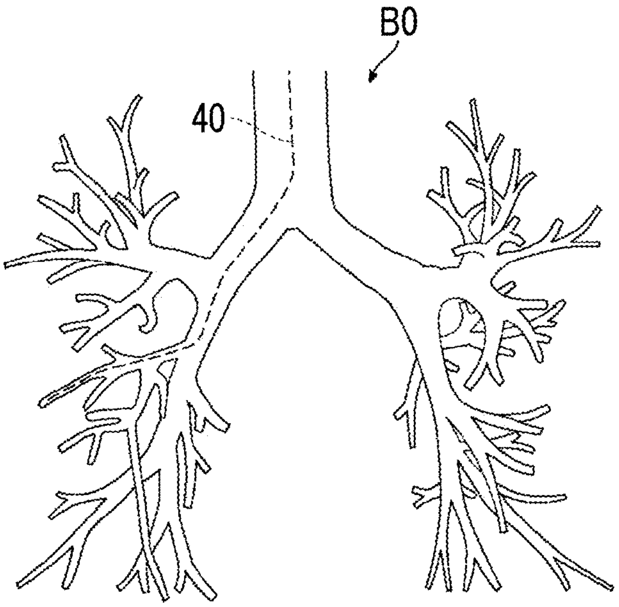
FIG. 5 is a diagram showing an example of a route in the bronchus image.

First, description of a method using surface rendering will be made as an example of the acquisition method of the virtual image K0 based on the three-dimensional image V0. As shown by a broken line in FIG. 6, the acquisition unit 11 extracts a bronchus structure from the acquired three-dimensional image V0 to generate a three-dimensional bronchus image B0. FIG. 4 shows an example of the three-dimensional bronchus image B0. FIG. 5 shows a route 40 of the endoscope set for the bronchus image B0. As the generation method of the three-dimensional bronchus image B0, a method described in, for example, JP2010-220742A can be applied as appropriate. The information on the route 40 may be, for example, input by a user using the operation unit 25, or may be predetermined in an imaging order or the like.

Next, the acquisition unit 11 sets each position at a predetermined interval along the route 40 as the viewpoint. These viewpoints are examples of a "virtual viewpoint predetermined in the three-dimensional image" according to the present disclosure.

Further, the acquisition unit 11 generates a projection image by performing the central projection of projecting the three-dimensional image V0 on a plurality of visual lines that extend radially in an insertion direction of the endoscope distal end 3B (that is, a direction toward a distal end of the bronchus) from each set viewpoint to a predetermined projection surface. This projection image is the virtual image K0 that is virtually generated as though the imaging is performed at the position of the endoscope distal end 3B. The acquisition unit 11 generates the virtual image K0 for each set viewpoint.

It should be noted that the acquisition unit 11 need only generate the virtual image K0 along at least the route 40, and can also generate, of course, the virtual image K0 not along the route 40. For example, the acquisition unit 11 may set each position in a region of the substantially entire bronchus as the viewpoint and generate the virtual image K0 at each position. Moreover, the acquisition unit 11 may select a part of the virtual image K0 generated in the region of substantially the entire bronchus along the route 40.

Method Using Volume Rendering

The method using the surface rendering has been described above. However, instead of method using the surface rendering, for example, a known volume rendering method or the like may be used to generate the virtual image K0. In the method using the volume rendering, the virtual image K0 as viewed from any virtual viewpoint set in the three-dimensional image V0 can be generated based on the pixel value, the CT value, and the like specified from the three-dimensional image V0. In this case, unlike the method using the surface rendering, the bronchus image B0 does not need to be generated, and the virtual image K0 can be directly generated from the three-dimensional image V0 as shown by a solid line in FIG. 6.

It should be noted that, in both the methods, an angle of view (range of visual line) of the virtual image K0 and the center (center in the projection direction) of the visual field are set in advance by input or the like from the user. In addition, a plurality of virtual images K0 at the viewpoints generated by the acquisition unit 11 are stored in, for example, the storage unit 22, the image storage server 5, and the like. It should be noted that, in the present embodiment, since the three-dimensional image is a CT image, the virtual image K0 may be a monochrome image generated based on the CT value that forms the CT image. In addition, the virtual image KG may be a monochrome image colored in a pseudo manner. Hereinafter, in FIGS. 9 to 15, an example is shown in which the virtual image K0 is directly generated from the three-dimensional image V0 by the method using the volume rendering. However, the present disclosure is not limited to this, and as in FIG. 6, the bronchus image B0 may be generated by the method using the surface rendering, and then the virtual image K0 may be generated.

Viewpoint difference estimation processing Description of the viewpoint difference estimation processing according to the present embodiment will be made with reference to FIGS. 6 to 8. The "viewpoint difference" is a misregistration amount between the virtual viewpoint P10 optionally set in the three-dimensional image V0 and the viewpoint P11 of the real image T0 (that is, the real position of the endoscope distal end 3B). For the sake of description, FIG. 7 shows the viewpoint difference ΔL between the virtual viewpoint P10 and the viewpoint P11 of the real image T0 on the bronchus image B0. It should be noted that the viewpoint difference estimation processing shown in FIG. 6 is merely an example, and can be modified as in various Examples described later.

Figure 6:
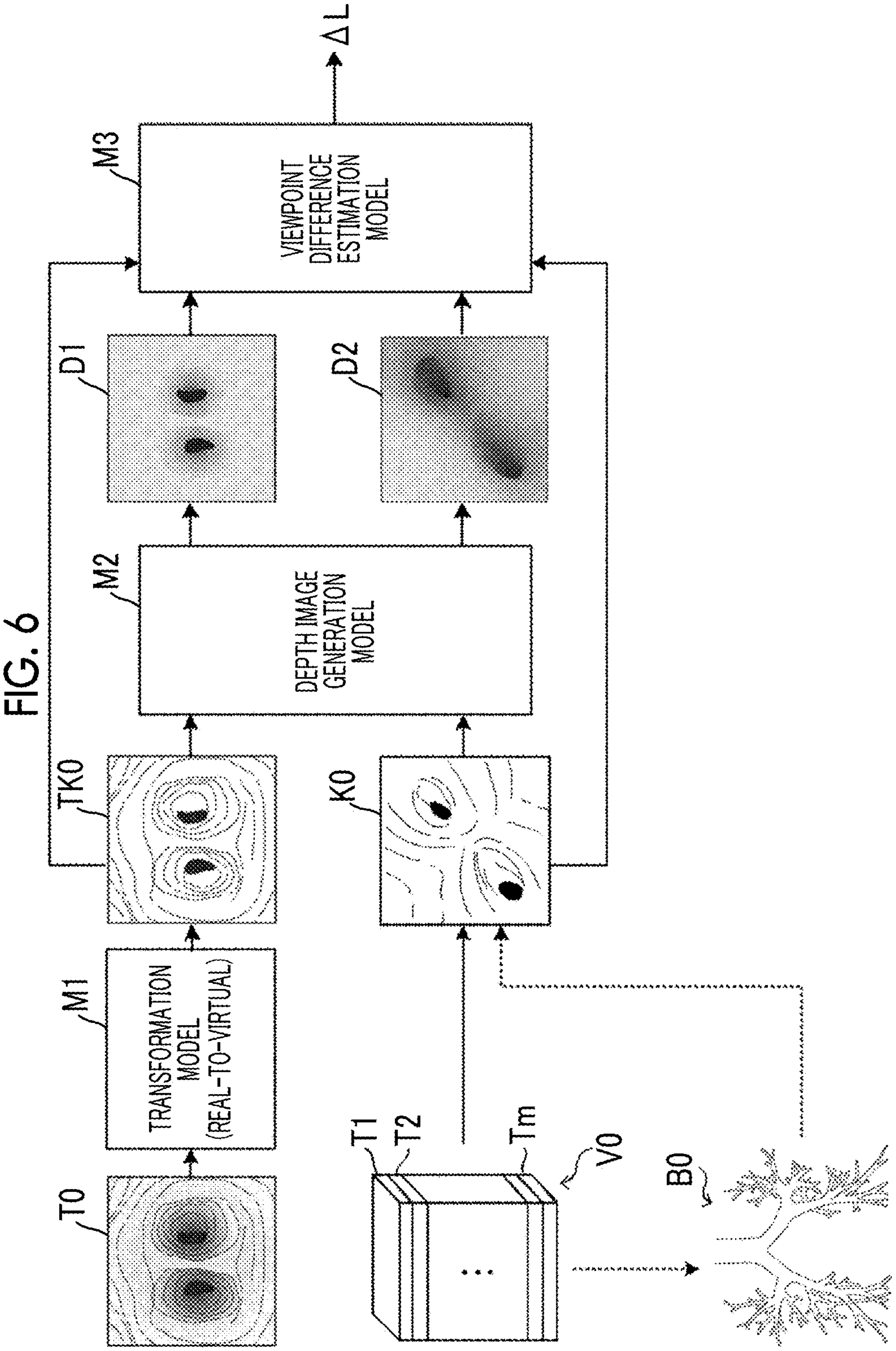
FIG. 6 is a diagram for describing an example of viewpoint difference estimation processing.
Figure 7:
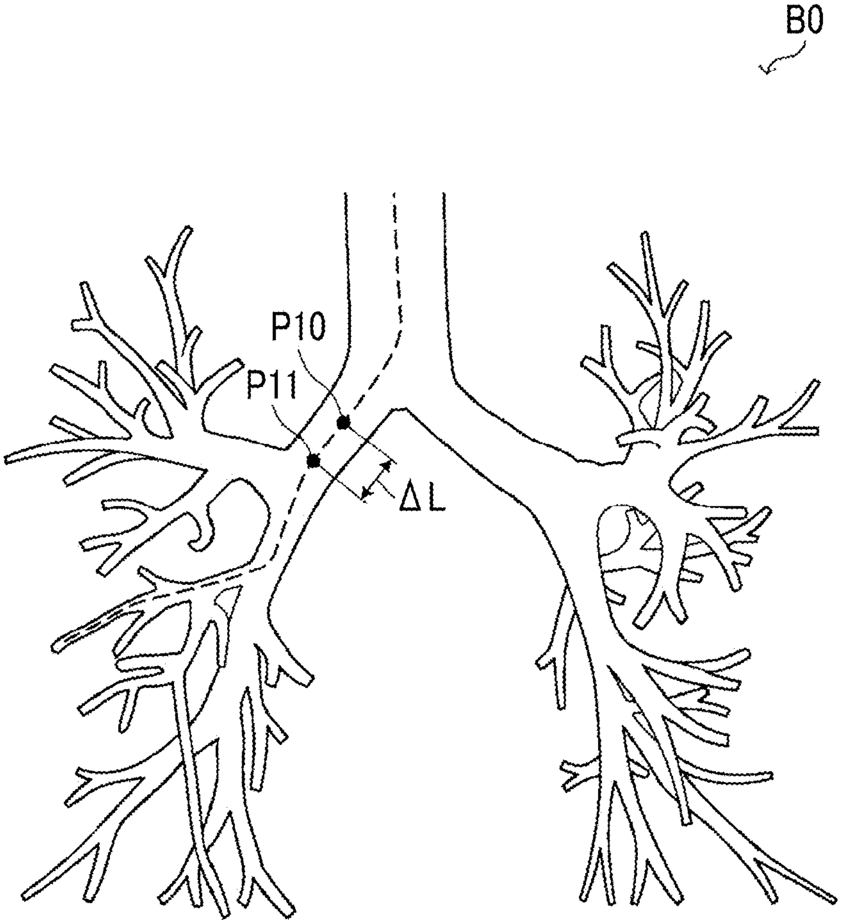
FIG. 7 is a diagram for describing a viewpoint difference.

As shown in FIG. 6, the transformation unit 12 transforms the real image T0 acquired by the acquisition unit 11 into a real-to-virtual transformed image TK0 having a virtual image style by using the transformation model M1. The transformation model M1 is a machine learning model that has been trained in advance to receive input of the real image, transform the input real image into the virtual image style, and output the transformed real image. Specifically, the transformation unit 12 inputs the real image T0 to the transformation model M1 to obtain the real-to-virtual transformed image TK0.

This transformation processing is performed to remove noise that is included in the real image T0 and is not included in the virtual image K0. Examples of such noise include noise caused by, for example, body fluids or the like adhering to a lens of the endoscope distal end 3B and fogging the lens, noise that cannot be captured by tomography but appears in the real image TO, and fine texture such as gloss and a blood vessel generated on the interior wall of the tubular structure. The "virtual image style" is an expression form in which these kinds of noise peculiar to the real image are removed, and is a so-called computer graphics (CG) style expression form. In the real-to-virtual transformed image TK0, it is desired that the noise included in the real image T0 is removed and the structure of the tubular structure in the real image T0 is not changed.

The generation unit 13 generates a first depth image D1 representing a distance for each pixel from the viewpoint P11 of the real image T0 to the interior wall of the tubular structure by using the depth image generation model M2. Similarly, the generation unit 13 generates a second depth image D2 representing a distance for each pixel from the virtual viewpoint P10 to the interior wall of the tubular structure by using the depth image generation model M2. The depth image generation model M2 is a machine learning model that has been trained in advance to receive input of an image representing the interior wall of the tubular structure and output a depth image representing a distance for each pixel from the viewpoint of the input image to the interior wall of the tubular structure.

The "depth image" represents a distance from the viewpoint position by the pixel value thereof. For example, in a case in which the pixel value is decreased as the distance from the viewpoint position is increased, the image is darker as the distance from the viewpoint position is increased. By setting a correlation between the pixel value of the depth image and the distance in advance, the distance from the viewpoint position can be calculated based on the pixel value of the depth image. It should be noted that the "distance from the viewpoint position" represented by the pixel value of the depth image is not limited to the distance from the viewpoint position itself, and may be represented by various values corresponding to the distance from the viewpoint position. For example, a viewpoint coordinate system having the viewpoint as an origin is set, the projection surface of the depth image is set in an XY plane, and a direction perpendicular to the projection surface (XY plane) is set as a Z direction. In this case, the "distance from the viewpoint position" may be simply represented by a distance in a Z-axis direction from the viewpoint (origin) (that is, a coordinate in the Z-axis direction). For example, the "distance from the viewpoint position" may be represented as a distance from the projection surface of the depth image.

In addition, the correlation between the pixel value of the depth image and the distance is not limited to the proportional relationship that the pixel value is decreased as the distance from the viewpoint position is increased, and may be determined by, for example, an inverse proportion or logarithmic proportion relationship. In addition, for example, although the pixel value is generally represented by 256 gradations of 8 bits in integers of 0 to 255 in many cases, the present disclosure is not limited to this, and the pixel value of the depth image may be represented by any value such as a negative number or a decimal number. The same applies to each of the depth images for training described later.

Specifically, the generation unit 13 inputs the real-to-virtual transformed image TK0 transformed from the real image T0 by the transformation unit 12 to the depth image generation model M2, to obtain the first depth image D1 at the viewpoint P11 of the real image T0. That is, it can be said that the first depth image D1 according to the present embodiment is an image generated based on the pixel value of the real-to-virtual transformed image TK0 obtained by transforming the real image T0 into the virtual image style.

In addition, the generation unit 13 obtains the second depth image D2 at the virtual viewpoint P10 by inputting the virtual image K0, which is generated from the three-dimensional image V0 acquired by the acquisition unit 11, at the virtual viewpoint P10, to the depth image generation model M2. That is, it can be said that the second depth image D2 according to the present embodiment is an image generated based on the pixel value of the virtual image K0.

The estimation unit 14 uses at least one of the real image T0 at the viewpoint P11 or the first depth image D1 and at least one of the virtual image K0 at the virtual viewpoint P10 or the second depth image D2, to estimate the viewpoint difference ΔL between the viewpoint P11 of the real image T0 and the virtual viewpoint P10. It should be noted that, in the estimation of the viewpoint difference ΔL, at least one of the first depth image D1 or the second depth image D2 is used.

As described above, a distance for each pixel from the viewpoint position to the interior wall of the tubular structure can be calculated based on the pixel value of the depth image. Therefore, since at least one of the first depth image D1 or the second depth image D2 is used, the viewpoint difference ΔL in the tubular structure having a three-dimensional structure can be estimated with higher accuracy than in a case in which the viewpoint difference ΔL is estimated by using only the real image T0, which is a two-dimensional image, and/or the virtual image K0.

Specifically, the estimation unit 14 estimates the viewpoint difference ΔL between the viewpoint P11 of the real image T0 and the viewpoint P10 of the virtual viewpoint by using the viewpoint difference estimation model M3. The viewpoint difference estimation model M3 is, for example, a machine learning model that has been trained in advance to at least receive input of at least one of the first depth image or the second depth image and output the viewpoint difference by using the input of at least one of the first depth image or the second depth image. In the example in FIG. 6, the viewpoint difference estimation model M3 also receives input of the real-to-virtual transformed image TK0 and the virtual image K0, in addition to the first depth image D1 and the second depth image D2. This is because it is considered that the accuracy of the viewpoint difference estimation model M3 is improved as the number of types of the input images is increased.

In the example in FIG. 6, the estimation unit 14 estimates the viewpoint difference ΔL between the viewpoint P11 of the real image T0 and the virtual viewpoint P10 by inputting the first depth image D1, the second depth image D2, the real-to-virtual transformed image TK0, and the virtual image K0 to the viewpoint difference estimation model M3. As described above, in the viewpoint difference estimation processing, the viewpoint difference ΔL may be estimated by indirectly using the real-to-virtual transformed image TK0 as the real image T0 instead of directly using the real image T0.

In addition, the estimation unit 14 may correct the position of the virtual viewpoint P10 so that the estimated viewpoint difference ΔL is reduced. For example, as shown in FIG. 7, in a case in which the virtual viewpoint P10 is retreated by ΔL from the viewpoint P11 (that is, the real position of the endoscope distal end 3B) of the real image T0 with respect to an entrance side of the bronchus, the estimation unit 14 sets the virtual viewpoint P10 to a position advanced by ΔL. In this way, an estimated position Pt of the endoscope distal end 3B in the tubular structure can be estimated by substantially matching the virtual viewpoint P10 with the viewpoint P11 of the real image T0.

It should be noted that the viewpoint difference ΔL may include a posture difference in addition to the misregistration amount. For example, the viewpoint difference ΔL may be represented by a displacement vector, a combination of the angle and the distance, an Euler angle, a rotation vector, or the like. Further, for example, the viewpoint difference ΔL may be represented by a relative posture between the virtual viewpoint P10 and the viewpoint P11 of the real image T0.

Figure 8:
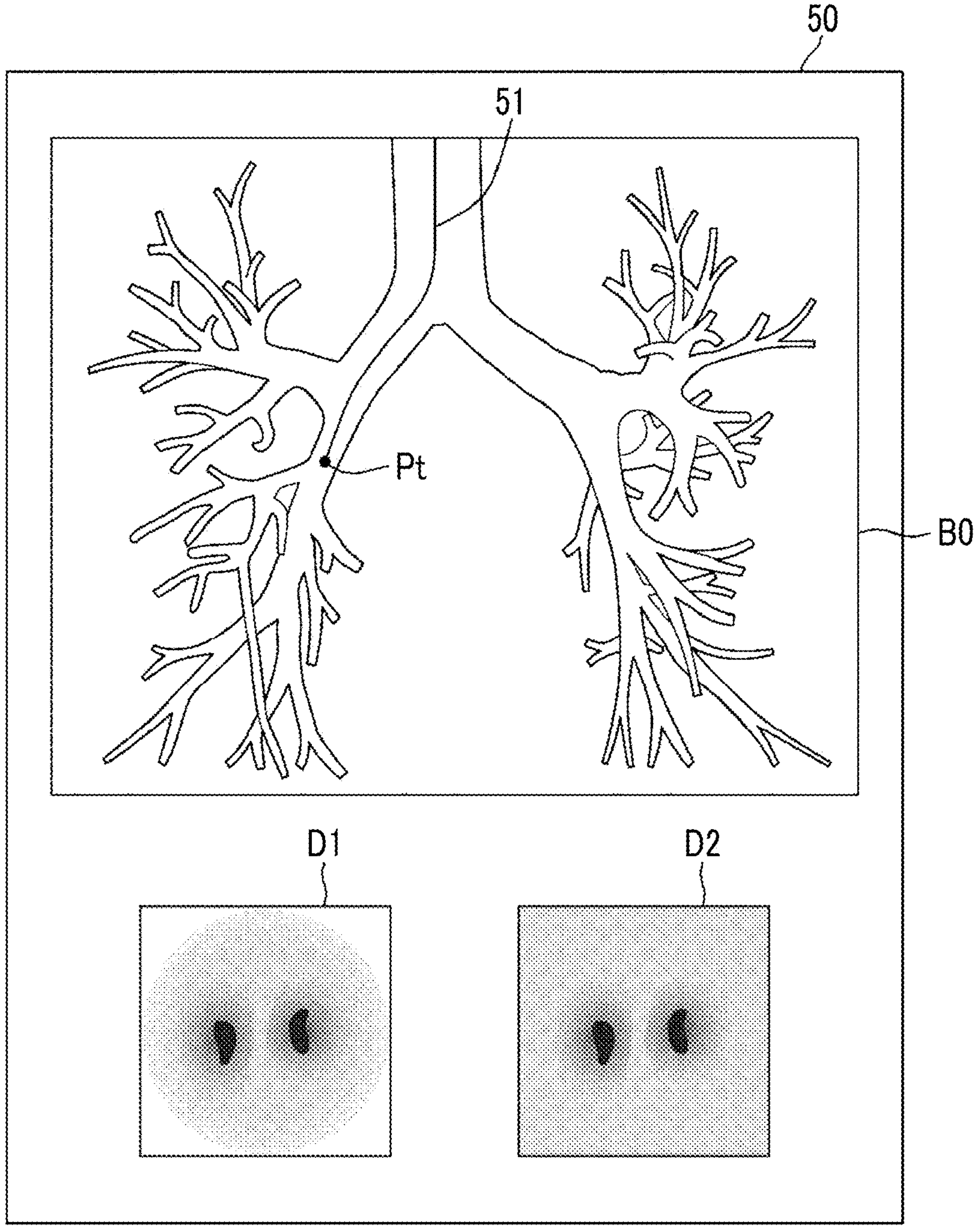
FIG. 8 is a diagram showing an example of a screen displayed on a display.

FIG. 8 shows an example of a screen 50 displayed on the display 24 by the controller 16. As shown in FIG. 8, the controller 16 may superimpose and display the estimated position Pt of the endoscope distal end 3B estimated by the estimation unit 14 and a movement track 51 of the endoscope distal end 3B, on the bronchus image B0. In addition, as shown in FIG. 8, the controller 16 may perform control of displaying the first depth image D1 based on the real image T0 at the estimated position Pt and the second depth image D2 based on the virtual image K0 at the estimated position Pt. In addition, the controller 16 may perform control of displaying the real image T0 and the virtual image K0 at the estimated position Pt on the display 24 (not shown).

As described above, the viewpoint difference estimation processing is performed. It should be noted that, as described above, the real image T0 constitutes one frame of the moving image. Therefore, the viewpoint difference estimation processing is repeatedly performed for each of the real images TO sequentially acquired in the moving image.

Training of Transformation Model M1

Next, description of a training method of the transformation model M1 used in the viewpoint difference estimation processing will be made using a plurality of methods. The training unit 15 trains the transformation model M1 by using at least one of the following methods.

First Training Method: Training Using GAN

Figure 9:
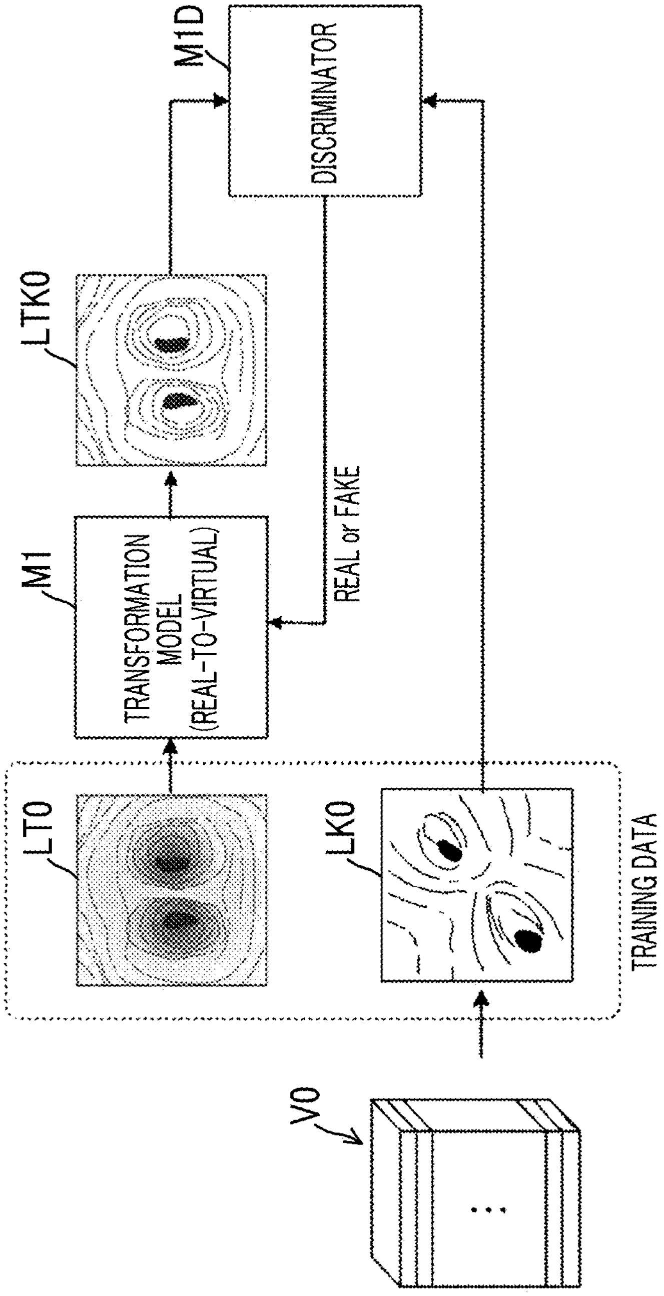
FIG. 9 is a diagram for describing an example of a training method of a transformation model.

FIG. 9 is a schematic diagram of the training method of the transformation model M1 obtained by a generative adversarial network (GAN) as an example. The GAN is a method of unsupervised learning in which a generator and a discriminator are included, the generator tries to generate fake data as close as possible to ground truth data, the discriminator tries to correctly discriminate the fake data, and the generator and the discriminator are trained in a mutually interactive manner.

The GAN of FIG. 9 is trained by using training data including a real image for training LT0, which is captured by the endoscope inserted into the tubular structure of the subject and which represents the interior wall of the tubular structure, and a virtual image for training LK0, which is generated based on the three-dimensional image V0 and which represents, in a pseudo manner, the interior wall of the tubular structure as viewed from the virtual viewpoint predetermined in the three-dimensional image V0. It should be noted that the three-dimensional image V0 as a generation source of the virtual image for training LK0 may be obtained by imaging the same subject as the subject of the real image for training LT0, or may be obtained by imaging a subject different from the subject of the real image for training LT0. That is, the real image for training LT0 and the virtual image for training LK0 may be non-pair data that are independent of each other.

The transformation model M1 corresponds to the generator in the GAN and is a machine learning model, such as a neural network, which transforms the input real image for training into an expression form close to the virtual image for training, which is the ground truth data, and outputs the transformed input image. A discriminator M1D is a machine learning model, such as a neural network, which discriminates whether the input image is the virtual image for training that is the ground truth (real) data or the real-to-virtual transformed image for training that is the fake data.

The training unit 15 generates a real-to-virtual transformed image for training LTK0 having an expression form close to the virtual image for training LK0, which is the ground truth data, by inputting the real image for training LT0 to the transformation model M1 (generator). In addition, the training unit 15 inputs any one of the real-to-virtual transformed image for training LTK0 generated by the transformation model M1 or the virtual image for training LK0, which is the ground truth data, to the discriminator M1D, to obtain the discrimination result. Then, the training unit 15 feeds back the discrimination result by the discriminator M1D and information indicating whether or not the discrimination result is correct to the transformation model M1 (generator). In this way, the transformation model M1 and the discriminator M1D are trained in a mutually interactive manner.

Second Training Method: Training Using CycleGAN

Figure 10:
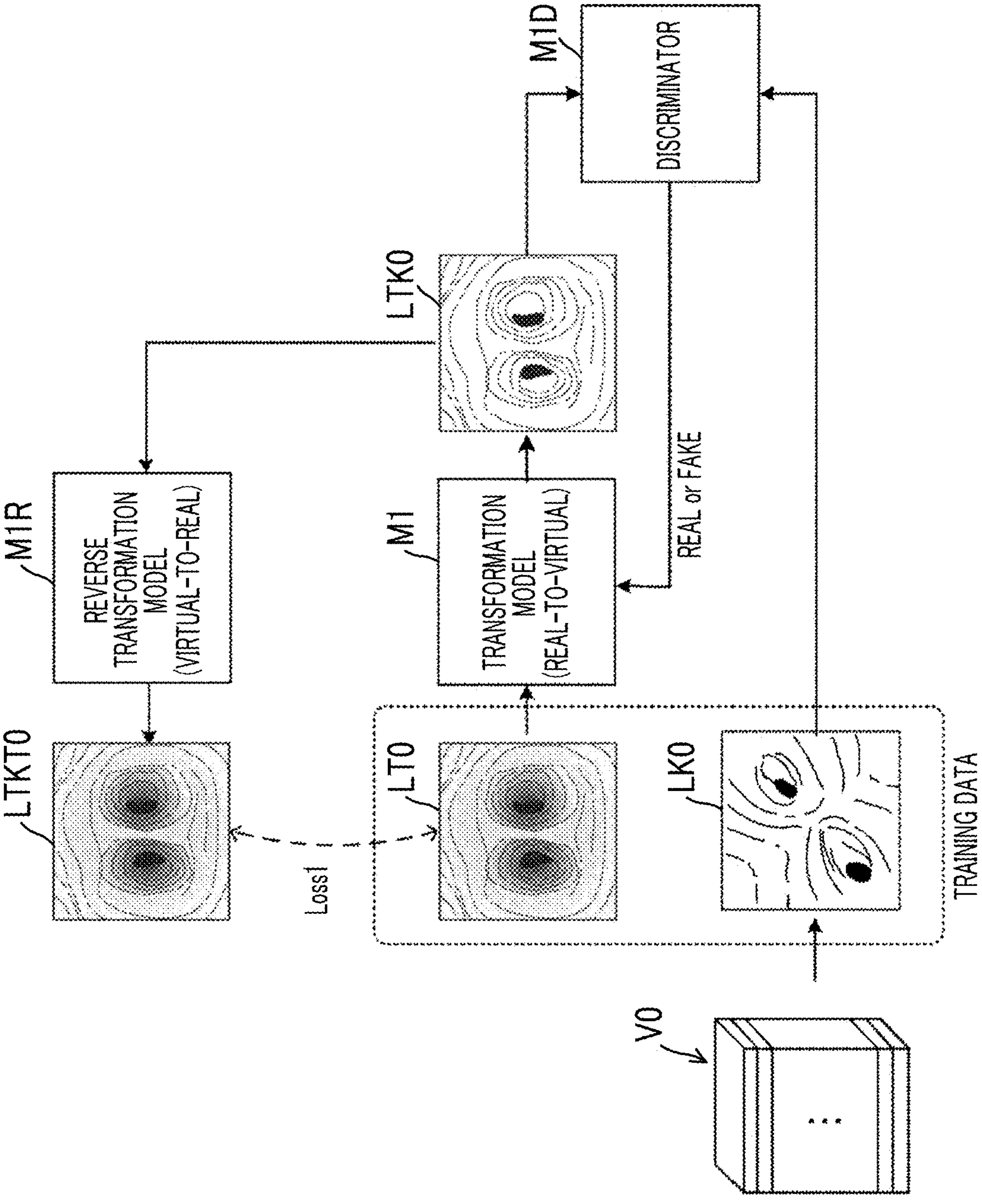
FIG. 10 is a diagram for describing an example of the training method of the transformation model.

FIG. 10 is a schematic diagram of the training method of the transformation model M1 obtained by a CycleGAN as another example. The CycleGAN is a method that enables accurate transformation without using pair data of a transformation source and a transformation target by learning a transformation function in a forward direction from the transformation source data to the transformation target data and a transformation function in a backward direction from the transformation target data to the transformation source data.

Although the first training method using the GAN can also perform training using the non-pair data, a constraint in the GAN is only that an expression form is the virtual image style. Therefore, even in a case in which the expression form is appropriately transformed before and after the transformation by the transformation model M1, there is a possibility that a problem occurs in which the bronchus structure in the image is inappropriately transformed.

In the second training method using the CycleGAN, a constraint is applied so that the data obtained by reverse transformation is returned to the original state. Therefore, it is possible to train the transformation model M1 while searching for pseudo pair data in which the bronchus structures are also similar in addition to the expression form. As a result, it is possible to generate the transformation model M1 in which the bronchus structure in the image is less likely to change, and it is possible to improve the accuracy of the transformation.

The CycleGAN in FIG. 10 includes a reverse transformation model M1R that reversely transforms the real-to-virtual transformed image for training having the virtual image style into a real-to-virtual-to-real transformed image for training having a real image style, in addition to the GAN in FIG. 9. The reverse transformation model M1R is a machine learning model, such as a neural network, corresponding to the generator in the backward direction in the CycleGAN.

The training unit 15 by inputting the real-to-virtual transformed image for training LTK0 output from the transformation model M1 to the reverse transformation model M1R. generates a real-to-virtual-to-real transformed image for training LTKT0 having a structure and an expression form which are close to the real image for training LT0 which is the original input data. In addition, the training unit 15 trains the transformation model M1 by using a loss function Loss1 including a degree of similarity between the real image for training LT0, which is the original input data, and the real-to-virtual-to-real transformed image for training LTKT0. The degree of similarity between the real image for training LT0 and the real-to-virtual-to-real transformed image for training LTKT0 is represented by, for example, a squared error for each pixel of each image, a squared error after normalizing the pixel value of each image, and a degree of similarity of cosines. In addition, for example, the degree of similarity is not limited to the degree of similarity between the pixel values themselves, and may be represented by a degree of similarity between the reciprocals of the pixel values and the logarithms of the pixel values.

Third Training Method: Training Using Depth Image

Figure 11:
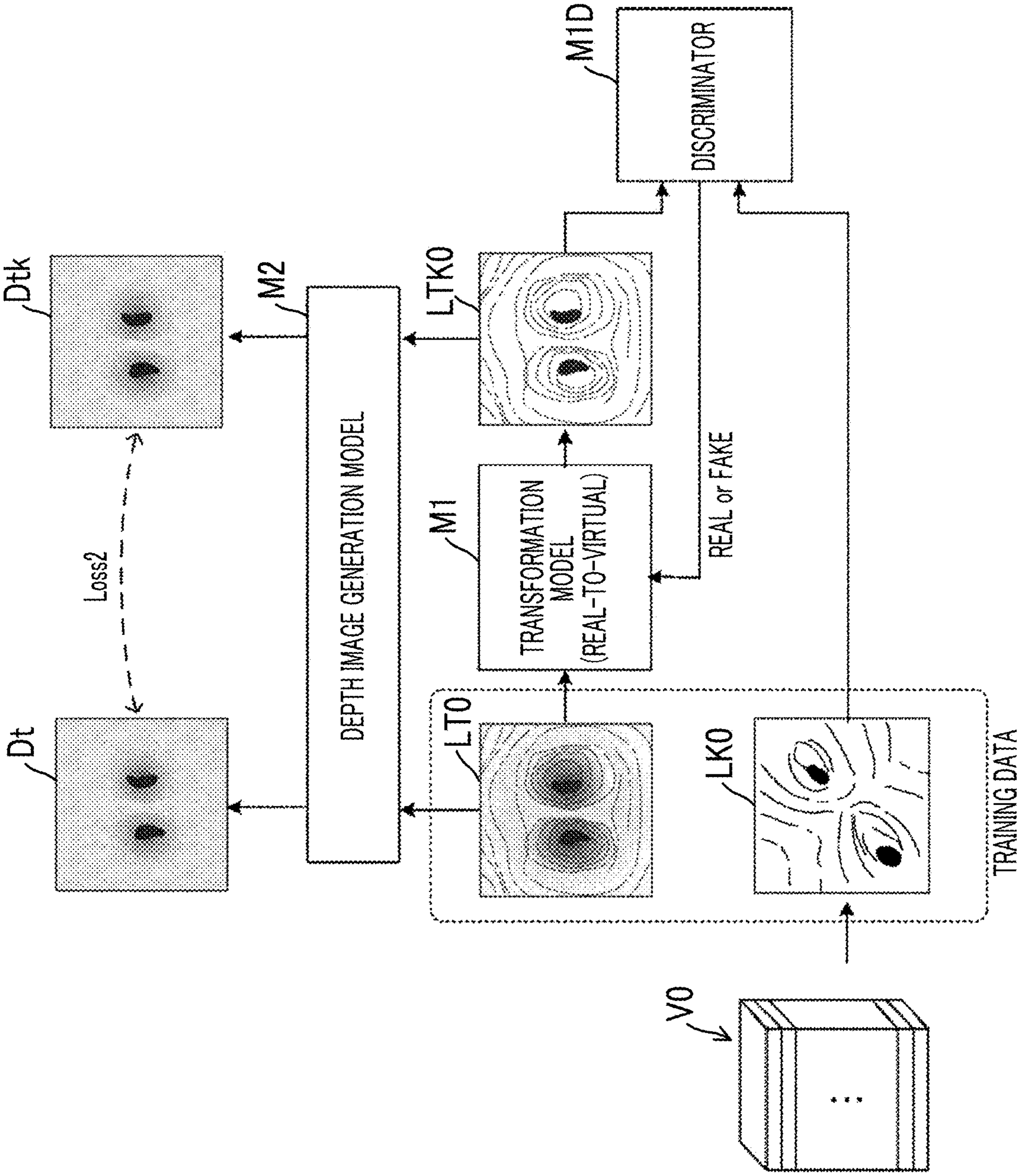
FIG. 11 is a diagram for describing an example of the training method of the transformation model.

FIG. 11 is a schematic diagram of the training method of the transformation model M1 using the depth image as still another example. As described above, in the first training method using the GAN, since only a constraint is applied so that the expression form is the virtual image style, there is a possibility that inappropriate transformation such as a change in the bronchus structure before and after the transformation by the transformation model M1 is performed. Therefore, in the third training method, the transformation model M1 is trained by using a loss function Loss2 including a degree of similarity between the depth images of the images before and after the transformation by the transformation model M1 based on the GAN of the first training method, thereby improving the accuracy of the transformation.

Specifically, first, the training unit 15 acquires an input image including any one of the real image for training or the virtual image for training. The "input image" here means an image that is input to the transformation model in the subsequent stage. In addition, the training unit 15 transforms the input image into a transformed image having an image style that is not included in the input image by using a transformation model trained to transform any one of the input real image for training or virtual image for training into an image style of the other of the input real image for training or virtual image for training.

In the example in FIG. 11, the training unit 15 acquires the input image including the real image for training LT0. In addition, the training unit 15 transforms the real image for training LT0 into the real-to-virtual transformed image for training LTK0 having the virtual image style by using the transformation model M1 trained to receive input of the real image for training, transform the input real image for training into the real-to-virtual transformed image for training having the virtual image style, and output the transformed real image for training.

In addition, the training unit 15 acquires an input depth image Dt representing a distance for each pixel from the viewpoint of the input image (real image for training LT0) to the interior wall of the tubular structure. Specifically, the training unit 15 generates the input depth image Dt by inputting the input image (real image for training LT0) to the depth image generation model M2.

Similarly, the training unit 15 acquires a transformed depth image Dtk representing a distance for each pixel from the viewpoint of the transformed image (real-to-virtual transformed image for training LTK0) to the interior wall of the tubular structure. Specifically, the training unit 15 generates the transformed depth image Dtk by inputting the transformed image (real-to-virtual transformed image for training LTK0) to the depth image generation model M2.

The training unit 15 trains the transformation model M1 by using the loss function Loss2 including a degree of similarity between the input depth image Dt and the transformed depth image Dtk. That is, the training unit 15 trains the transformation model M1 so that the transformed depth image Dtk approximates the input depth image Dt. The degree of similarity between the input depth image Dt and the transformed depth image Dtk is represented by, for example, a squared error for each pixel of each image, a squared error after normalizing the depth (pixel value) of each image, and a degree of similarity of cosines. In addition, for example, the degree of similarity is not limited to the degree of similarity between the pixel values themselves, and may be represented by a degree of similarity between the reciprocals of the pixel values and the logarithms of the pixel values.

As described above, with the training method of the transformation model M1 using the loss function Loss2 including the degree of similarity between the depth images, the transformation model M1 can be trained while searching for the pseudo pair data by applying a constraint so that the depth images before and after the transformation approximate each other. Therefore, it is possible to generate the transformation model M1 in which the bronchus structure in the image is less likely to change, and it is possible to improve the accuracy of the transformation.

It should be noted that, from a viewpoint of ease of preparation of the training data, it is desired that the depth image generation model M2 is trained based on the virtual image generated based on the three-dimensional image (details will be described later). The inventors have found that a good depth image can be obtained even in a case in which the real image is input to the depth image generation model M2 that has been trained based on the virtual image. Therefore, in the present method, the input depth image Dt of the real image for training LT0 is obtained by using, in another use, the depth image generation model M2 that has been trained based on the virtual image. With such a form, it is possible to save the time and effort of creating the depth image generation model that has been trained for the real image.

Fourth Training Method: Supervised Learning

In the first to third training methods, the method of the unsupervised learning using the non-pair data as the training data has been described. On the other hand, supervised learning can also be applied by specifying the real position of the endoscope distal end 3B in the tubular structure by the electromagnetic sensor or the like and using the pair data of the real image and the virtual image having the same viewpoint. In this case, the training unit 15 performs supervised learning on the transformation model M1 by using the training data including a combination of the real image for training and the virtual image for training that are specified to have the same viewpoint.

It should be noted that, in general, it is difficult to prepare a large amount of such pair data. Therefore, the training unit 15 may train the transformation model M1 by combining the first to fourth training methods as appropriate.

Training of Reverse Transformation Model M1R

So far, the form has been described in which the real image is transformed into the real-to-virtual transformed image having the virtual image style, but the technique of the present disclosure can also be applied to a form in which the virtual image is transformed into a virtual-to-real transformed image having the real image style. That is, it is also possible to apply the first to fourth training methods related to the training of the transformation model M1 in another use, to generate the reverse transformation model M1R trained to receive input of the virtual image, transform the input virtual image into the real image style, and output the transformed virtual image.

The reverse transformation model M1R can be generated by replacing the real image for training LT0 and the virtual image for training LK0 in the first to fourth training methods related to the training of the transformation model M1. That is, the input image to the reverse transformation model M1R in a training phase includes the virtual image for training LK0.

Training of Depth Image Generation Model M2

Next, description of a training method of the depth image generation model M2 used in the viewpoint difference estimation processing will be made using a plurality of methods. The training unit 15 trains the depth image generation model M2 by using at least one of the following methods. Hereinafter, since the depth image generation models M2 obtained by the training methods receive input of different types of data, the depth image generation models M2 will be separately referred to as depth image generation models M2A to M2C.

First Training Method: Training Using Virtual Image and Depth Image

Figure 12:
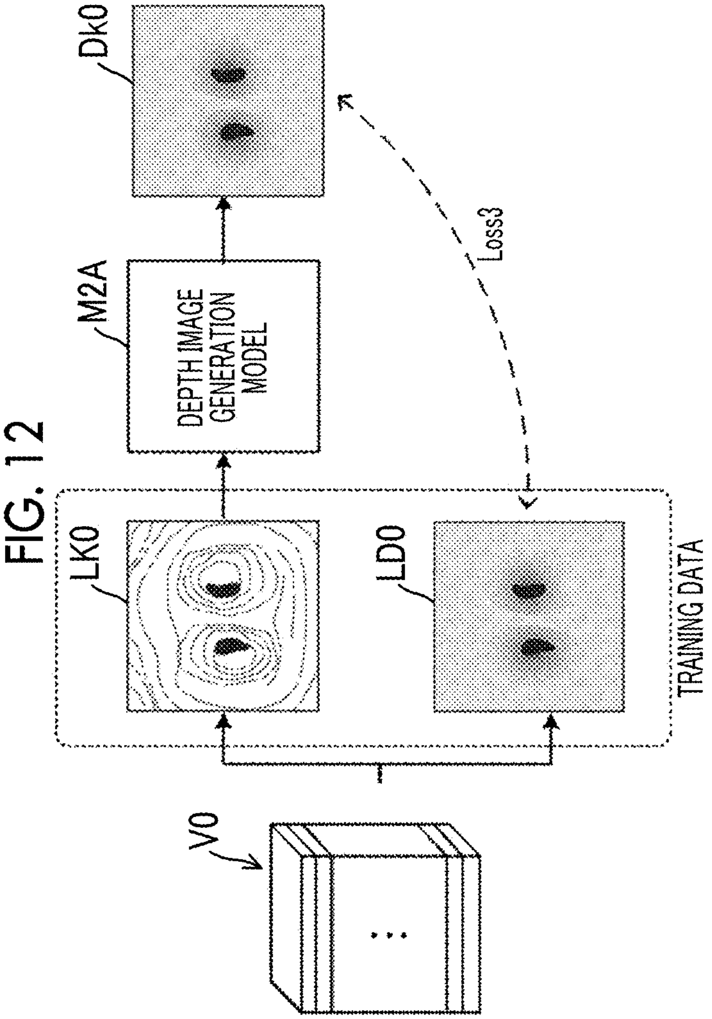
FIG. 12 is a diagram for describing an example of a training method of a depth image generation model.

FIG. 12 is a schematic diagram of a training method of the depth image generation model M2A obtained by supervised learning as an example. As shown in FIG. 12, the depth image generation model M2A is trained by using training data including a combination (pair data) of the virtual image for training LK0 and a depth image for training LD0.

Here, the virtual image for training LK0 is an image, which is generated based on the three-dimensional image V0 of the subject and which represents, in a pseudo manner, the interior wall of the tubular structure as viewed from a virtual viewpoint P4 predetermined in the three-dimensional image V0. The depth image for training LD0 is an image, which is generated based on distance information from the virtual viewpoint P4 in the three-dimensional image V0 to the interior wall of the tubular structure and which represents a distance for each pixel from the virtual viewpoint P4 to the interior wall of the tubular structure, and is the ground truth data. The virtual viewpoint P4 is an example of a fourth viewpoint according to the present disclosure.

The distance information indicates, for example, a distance from the virtual viewpoint P4 in the three-dimensional image V0 to a point at which an opacity is equal to or greater than a predetermined value. In a case in which the opacity is equal to or greater than the predetermined value in the three-dimensional image V0, it is considered that the portion corresponds to the interior wall of the tubular structure. In addition, for example, the distance information may indicate a distance from the virtual viewpoint P4 to a surface of the bronchus image B0 in a case in which the bronchus image B0 is generated based on the three-dimensional image V0 and then the virtual image for training LK0 is generated (in a case in which the virtual image for training LK0 is generated by the surface rendering).

The depth image generation model M2A is a machine learning model, such as a neural network, which transforms the input virtual image for training into the depth image and outputs the depth image. The training unit 15 generates a depth image Dk0 having an expression form close to the depth image for training LD0, which is the ground truth data, by inputting the virtual image for training LK0 to the depth image generation model M2A.

In addition, the training unit 15 trains the depth image generation model M2A by using a loss function Loss3 including a degree of similarity between the depth image Dk0 generated by the depth image generation model M2A and the depth image for training LD0 which is the ground truth data. The degree of similarity between the depth image Dk0 and the depth image for training LD0 is represented by, for example, a squared error for each pixel of each image, a squared error after normalizing the pixel value of each image, and a degree of similarity of cosines. In addition, for example, the degree of similarity is not limited to the degree of similarity between the pixel values themselves, and may be represented by a degree of similarity between the reciprocals of the pixel values and the logarithms of the pixel values.

As described above, the depth image generation model M2A obtained by the first training method can prepare the pair data for training (virtual image for training LK0 and depth image for training LD0) based on the virtual image based on the three-dimensional image V0. Therefore, it is easy to prepare the data for training as compared with other methods.

Figure 13:
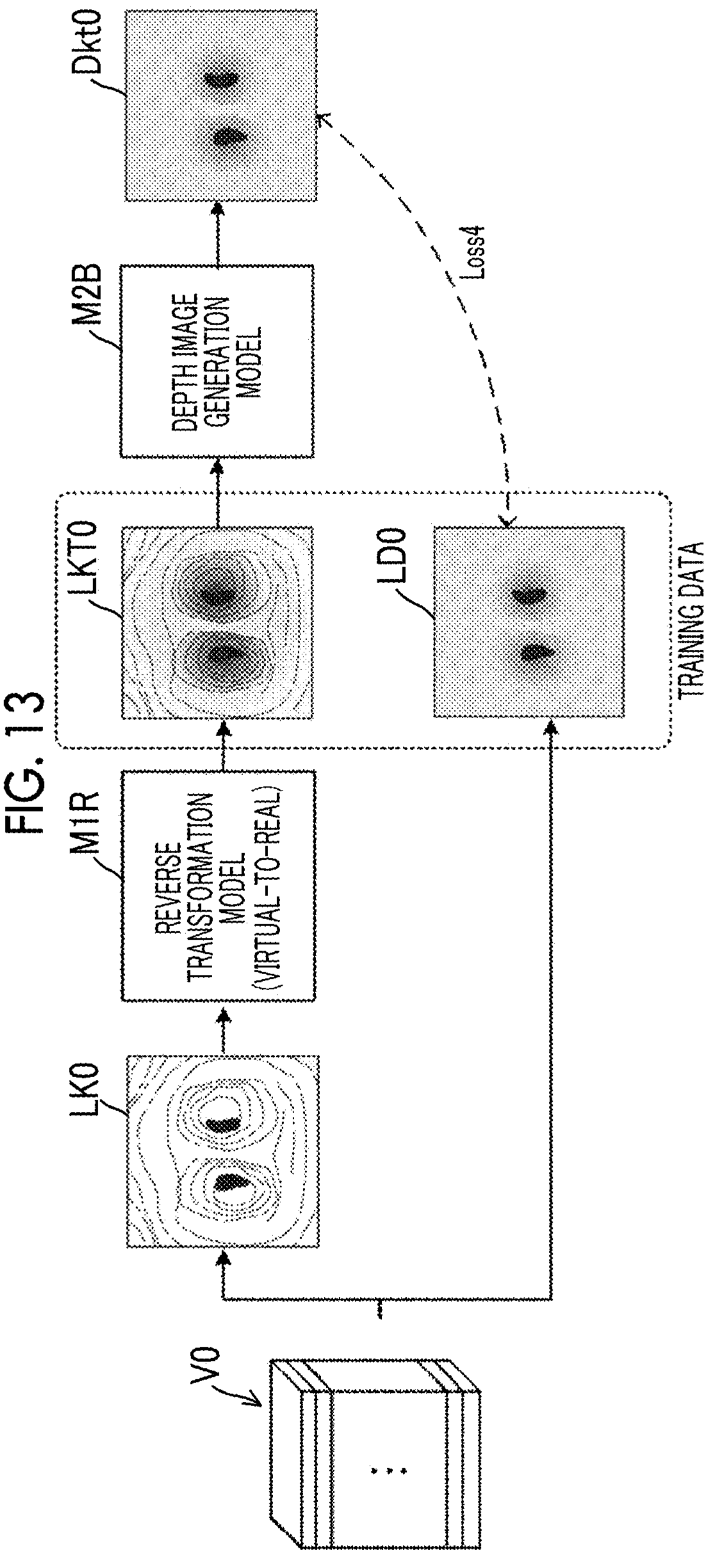
FIG. 13 is a diagram for describing an example of the training method of the depth image generation model.

Second Training Method: Training Using Virtual-to-Real Transformed Image and Depth Image FIG. 13 is a schematic diagram of a training method of the depth image generation model M2B obtained by supervised learning as another example. As shown in FIG. 13, the depth image generation model M2B is trained by using training data including a combination (pair data) of a virtual-to-real transformed image for training LKT0, which is obtained by transforming the virtual image for training LK0 into the real image style by using the reverse transformation model M1R, and the depth image for training LD0.

Here, the virtual image for training LK0 is an image, which is generated based on the three-dimensional image V0 of the subject and which represents, in a pseudo manner, the interior wall of the tubular structure as viewed from a virtual viewpoint P5 predetermined in the three-dimensional image V0. As described above, the reverse transformation model M1R is a machine learning model that has been trained in advance to receive input of the virtual image, transform the input virtual image into the real image style, and output the transformed virtual image. The depth image for training LD0 is an image, which is generated based on distance information from the virtual viewpoint P5 in the three-dimensional image V0 to the interior wall of the tubular structure and which represents a distance for each pixel from the virtual viewpoint P5 to the interior wall of the tubular structure, and is the ground truth data. The virtual viewpoint P5 is an example of a fifth viewpoint according to the present disclosure. Since the distance information is the same as the distance information in the first training method, the description thereof will be omitted.

The depth image generation model M2B is a machine learning model, such as a neural network, which transforms the input virtual-to-real transformed image for training into the depth image and outputs the depth image. The training unit 15 generates a depth image Dkt0 having an expression form close to the depth image for training LD0, which is the ground truth data, by inputting the virtual-to-real transformed image for training LKT0 to the depth image generation model M2B.

In addition, the training unit 15 trains the depth image generation model M2B by using a loss function Loss4 including a degree of similarity between the depth image Dkt0 generated by the depth image generation model M2B and the depth image for training LD0 which is the ground truth data. The degree of similarity between the depth image Dkt0 and the depth image for training LD0 is represented by, for example, a squared error for each pixel of each image, a squared error after normalizing the pixel value of each image, and a degree of similarity of cosines. In addition, for example, the degree of similarity is not limited to the degree of similarity between the pixel values themselves, and may be represented by a degree of similarity between the reciprocals of the pixel values and the logarithms of the pixel values.

The depth image generation model M2B obtained as described above causes the time and effort of transforming the virtual image for training LK0 into the virtual-to-real transformed image for training LKT0 as compared with the first training method. On the other hand, in the operational phase, the accuracy can be maintained even in a case in which the real image T0 is used as the input to the depth image generation model M2B.

Third Training Method: Training Using Real Image and Depth Image

Figure 14:
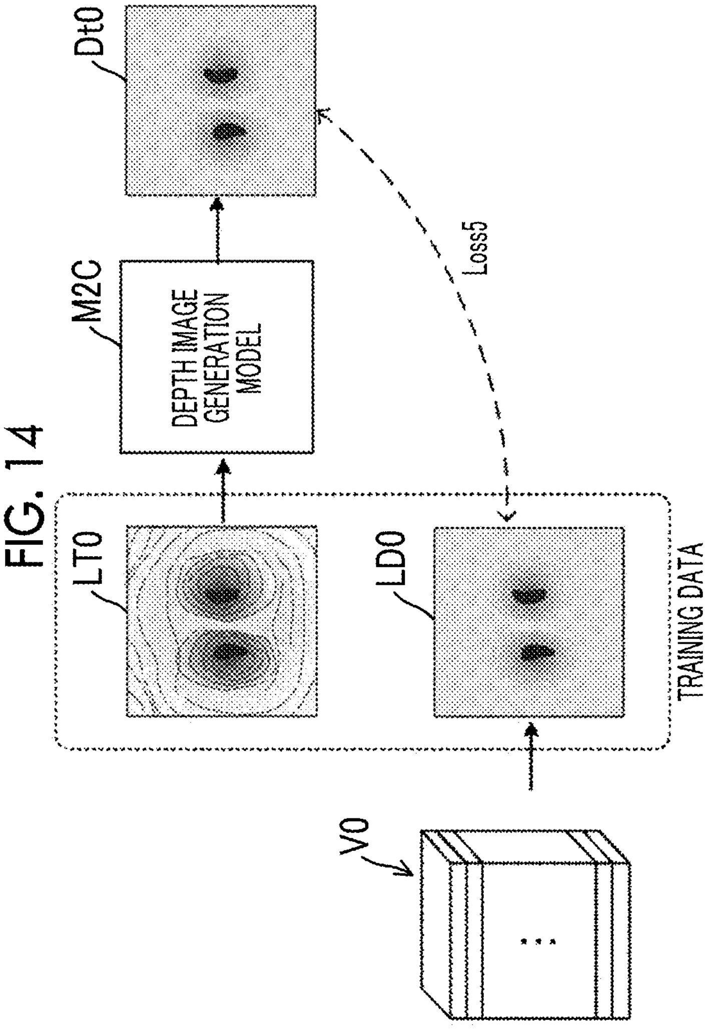
FIG. 14 is a diagram for describing an example of the training method of the depth image generation model.

FIG. 14 is a schematic diagram of a training method of the depth image generation model M2C obtained by supervised learning as still another example. As shown in FIG. 14, the depth image generation model M2C is trained by using training data including a combination (pair data) of the real image for training LT0, which is captured by the endoscope inserted into the tubular structure of the subject and which represents the interior wall of the tubular structure, and the depth image for training LD0, which represents a distance for each pixel from a viewpoint corresponding to a viewpoint at which the real image for training LT0 is captured to the interior wall of the tubular structure.

Here, the depth image for training LD0 is generated based on the distance information from the viewpoint corresponding to the viewpoint at which the real image for training LT0 is captured, in the three-dimensional image V0 of the subject, to the interior wall of the tubular structure, and is used as the ground truth data. The viewpoint corresponding to the viewpoint at which the real image for training LT0 is captured, in the three-dimensional image V0, that is, the real position of the endoscope distal end 3B in the inside of the tubular structure can be specified by, for example, the electromagnetic sensor or the like provided in the endoscope distal end 3B that captures the real image for training LT0.

Since the distance information is the same as the distance information in the first training method, the description thereof will be omitted.

The depth image generation model M2C is a machine learning model, such as a neural network, which transforms the input REAL image for training into the depth image and outputs the depth image. The training unit 15 generates a depth image Dt0 having an expression form close to the depth image for training LD0, which is the ground truth data, by inputting the real image for training LT0 to the depth image generation model M2C.

In addition, the training unit 15 trains the depth image generation model M2C by using a loss function Loss5 including a degree of similarity between the depth image Dt0 generated by the depth image generation model M2C and the depth image for training LD0 which is the ground truth data. The degree of similarity between the depth image Dt0 and the depth image for training LD0 is represented by, for example, a squared error for each pixel of each image, a squared error after normalizing the pixel value of each image, and a degree of similarity of cosines. In addition, for example, the degree of similarity is not limited to the degree of similarity between the pixel values themselves, and may be represented by a degree of similarity between the reciprocals of the pixel values and the logarithms of the pixel values.

Since the depth image generation model M2C obtained as described above needs to specify the viewpoint corresponding to the viewpoint at which the real image for training LT0 is captured, in the three-dimensional image V0, that is, the real position of the endoscope distal end 3B in the inside of the tubular structure, as the training data, it is difficult to prepare the training data. On the other hand, in the operational phase, higher accuracy can be maintained even in a case in which the real image T0 is used as the input to the depth image generation model M2*c*.

Modification Example

In the first to third training methods, it has been described that the depth image for training LD0 is generated based on the distance information derived based on the three-dimensional image V0, but the present disclosure is not limited to this. The depth image for training LD0 may be generated, for example, based on an actual measurement value of the distance from the viewpoint at which the real image for training LT0 is captured to the interior wall of the tubular structure, the actual measurement value being obtained by a distance-measuring sensor mounted on the endoscope distal end 3B or the like. As the distance-measuring sensor, for example, various depth sensors, such as a time of flight (ToF) camera, can be used.

The depth image for training LD0 based on the actual measurement value obtained by the distance-measuring sensor is more accurate although it is difficult to prepare the data. Therefore, the accuracy of each of the depth image generation models M2A to M2C can be improved.

Training of Viewpoint Difference Estimation Model M3

Next, description of a training method of the viewpoint difference estimation model M3 used in the viewpoint difference estimation processing of FIG. 6 will be made with reference to FIG. 15. The viewpoint difference estimation model M3 is a machine learning model, such as a neural network, which uses at least one of the real image T0 or the first depth image D1 based on the real image T0, and at least one of the virtual image K0 or the second depth image D2 based on the virtual image K0, to estimate the viewpoint difference ΔL between the virtual image K0 and the real image T0. As the training data for the learning model, for example, it is considered to prepare the virtual image K0, the real image T0, and the ground truth data of the viewpoint difference ΔL between the virtual image K0 and the real image T0, but it is difficult to prepare a combination of the virtual image K0 and the real image T0 of which the viewpoint difference ΔL is known.

Therefore, the viewpoint difference estimation model M3 according to the present embodiment is trained through supervised learning using training data including a combination of at least one of a first virtual image for training as viewed from the virtual viewpoint P1 predetermined in the three-dimensional image V0 or a first depth image for training representing a distance for each pixel from the virtual viewpoint P1 to the interior wall of the tubular structure, at least one of a second virtual image for training as viewed from the virtual viewpoint P2 that is predetermined in the three-dimensional image V0 and is different from the virtual viewpoint P1 or a second depth image for training representing a distance for each pixel from the virtual viewpoint P2 to the interior wall of the tubular structure, and a viewpoint difference ΔL0 between the virtual viewpoint P1 and the virtual viewpoint P2. Here, each of the first virtual image for training and the second virtual image for training is generated based on the three-dimensional image V0 of the subject. The virtual viewpoint P1 is an example of a first viewpoint according to the present disclosure. The virtual viewpoint P2 is an example of a second viewpoint according to the present disclosure.

Figure 15:
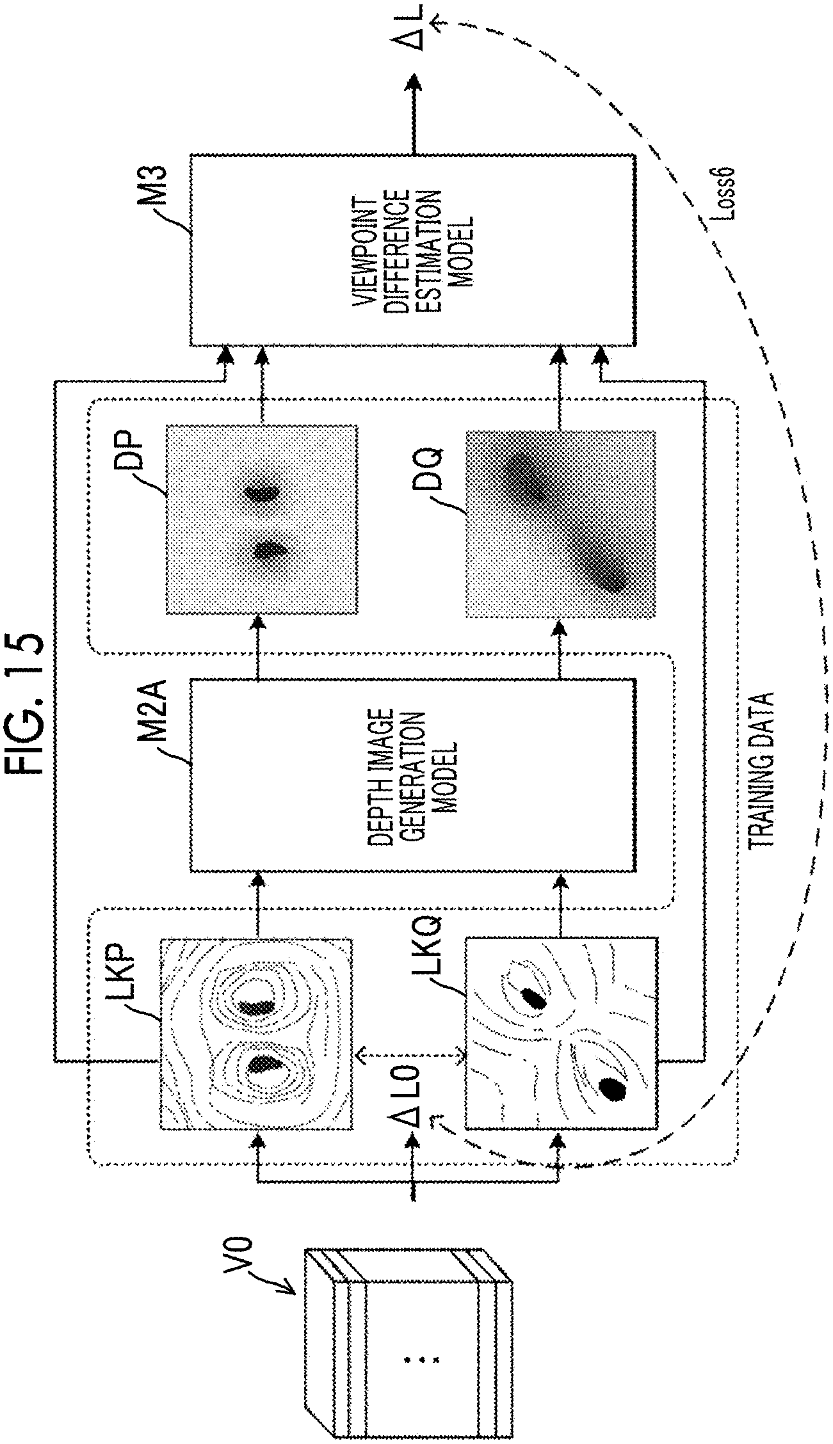
FIG. 15 is a diagram for describing an example of a training method of a viewpoint difference estimation model.

For example, the viewpoint difference estimation model M3 in the example of FIG. 15 is trained through supervised learning using training data including a combination of a virtual image for training LKP which represents, in a pseudo manner, the interior wall of the tubular structure as viewed from the virtual viewpoint P1, a virtual image for training LKQ which represents, in a pseudo manner, the interior wall of the tubular structure as viewed from the virtual viewpoint P2, and the viewpoint difference ΔL0 between the virtual viewpoint P1 and the virtual viewpoint P2. In this case, since the virtual viewpoints P1 and P2 in the three-dimensional image V0 are known, the viewpoint difference ΔL0 between the virtual viewpoints P1 and P2 can also be generated based on the three-dimensional image V0 of the subject.

Specifically, the training unit 15 first generates a depth image DP by inputting the virtual image for training LKP generated based on the three-dimensional image V0 of the subject to the depth image generation model M2A. That is, the depth image DP is an image representing the distance for each pixel from the virtual viewpoint P1 to the interior wall of the tubular structure. Similarly, the training unit 15 generates a depth image DQ by inputting the virtual image for training LKQ generated based on the three-dimensional image V0 of the subject to the depth image generation model M2A. That is, the depth image DQ is an image representing the distance for each pixel from the virtual viewpoint P2 to the interior wall of the tubular structure.

Thereafter, the training unit 15 inputs the virtual images for training LKP and LKQ and the depth images DP and DQ to the viewpoint difference estimation model M3, to obtain the estimated viewpoint difference ΔL. In addition, the training unit 15 trains the viewpoint difference estimation model M3 by using a loss function Loss6 including a degree of similarity between the estimated viewpoint difference ΔL estimated by the viewpoint difference estimation model M3 and the viewpoint difference ΔL0 between the virtual viewpoint P1 and the virtual viewpoint P2, which are the ground truth data.

EXAMPLES

Although the example of the viewpoint difference estimation processing has been described above, the technique of the present disclosure is not limited to this, and various Examples shown below are also included. All of the following examples have a common point in that the viewpoint difference estimation processing of estimating the viewpoint difference ΔL between the viewpoint P11 of the real image T0 and the virtual viewpoint P10 is performed. On the other hand, a combination and the contents of the transformation model M1, the reverse transformation model M1R, the depth image generation models M2A to M2C, and the viewpoint difference estimation model M3 used in the viewpoint difference estimation processing are different from those in the viewpoint difference estimation processing. Hereinafter, description of various Examples will be made with reference to FIGS. 16 to 36. In FIGS. 16 to 36, an upper side of a broken line represents processing in the operational phase, and a lower side of a broken line represents processing in the training phase.

First, description of Examples 1-1 to 1-4 will be made. In Examples, training is performed in the training phase by using two virtual images for training LKP and LKQ, and the viewpoint difference ΔL is estimated in the operational phase based on two depth images D1 and D2. In this case, there is an advantage that the ground truth data is accurate and easy to prepare. In Examples 1-1 to 1-4, the virtual image for training LKP is an example of a first virtual image for training according to the present disclosure, and the virtual image for training LKQ is an example of a second virtual image for training according to the present disclosure. In addition, the depth image DP is an example of a first depth image for training according to the present disclosure, and the depth image DQ is an example of a second depth image for training according to the present disclosure.

Example 1-1

Figure 16:
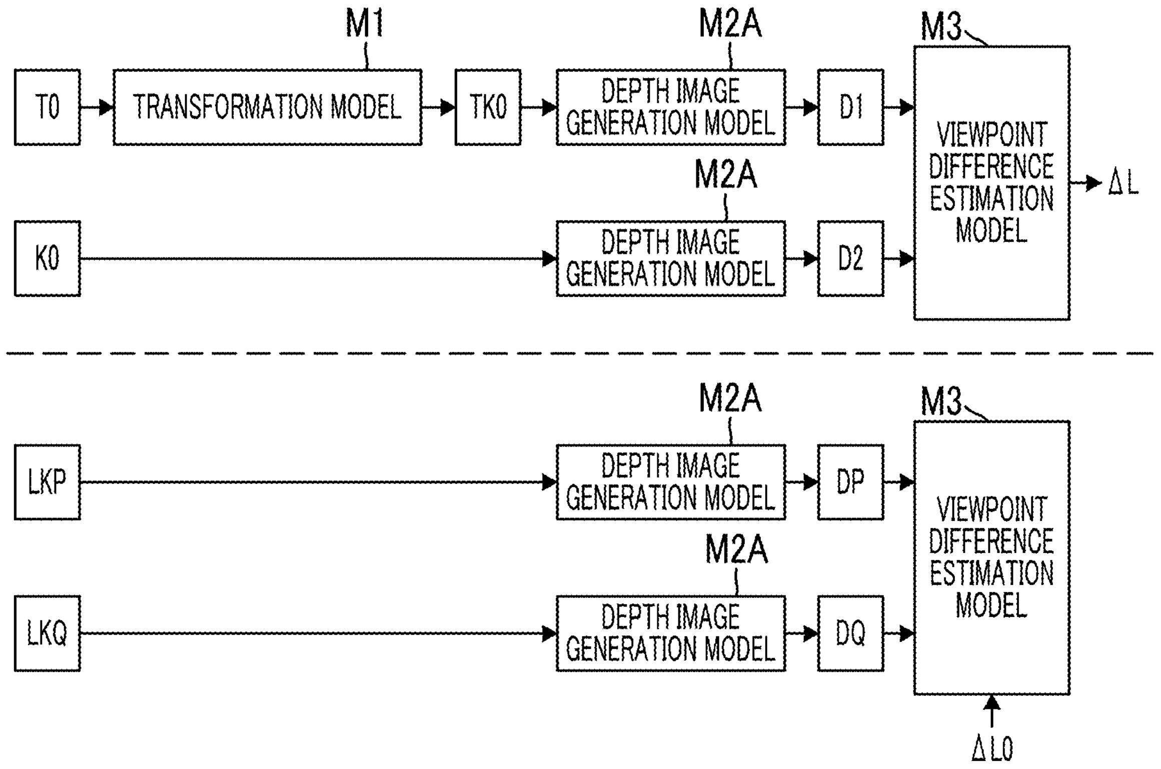
FIG. 16 is a diagram showing contents of viewpoint difference estimation processing according to Example 1-1.

FIG. 16 shows an overview of viewpoint difference estimation processing according to Example 1-1. In the training phase in the present example, the training unit 15 generates the depth image DP by inputting the virtual image for training LKP as viewed from the virtual viewpoint P1 to the depth image generation model M2A. Further, the training unit 15 generates the depth image DQ by inputting the virtual image for training LKQ as viewed from the virtual viewpoint P2 to the depth image generation model M2A. In addition, the training unit 15 trains the viewpoint difference estimation model M3 by using, as training data, the viewpoint difference ΔL0 between the virtual viewpoint P1 and the virtual viewpoint P2, and the depth images DP and DQ.

In the operational phase in the present example, the transformation unit 12 transforms the real image T0 into the real-to-virtual transformed image TK0 by inputting the real image T0 to the transformation model M1. The generation unit 13 generates the first depth image D1 by inputting the real-to-virtual transformed image TK0 to the depth image generation model M2A. In addition, the generation unit 13 generates the second depth image D2 by inputting the virtual image K0 to the depth image generation model M2A. The estimation unit 14 estimates the viewpoint difference ΔL by inputting the first depth image D1 and the second depth image D2 to the viewpoint difference estimation model M3.

Example 1-2

Figure 17:
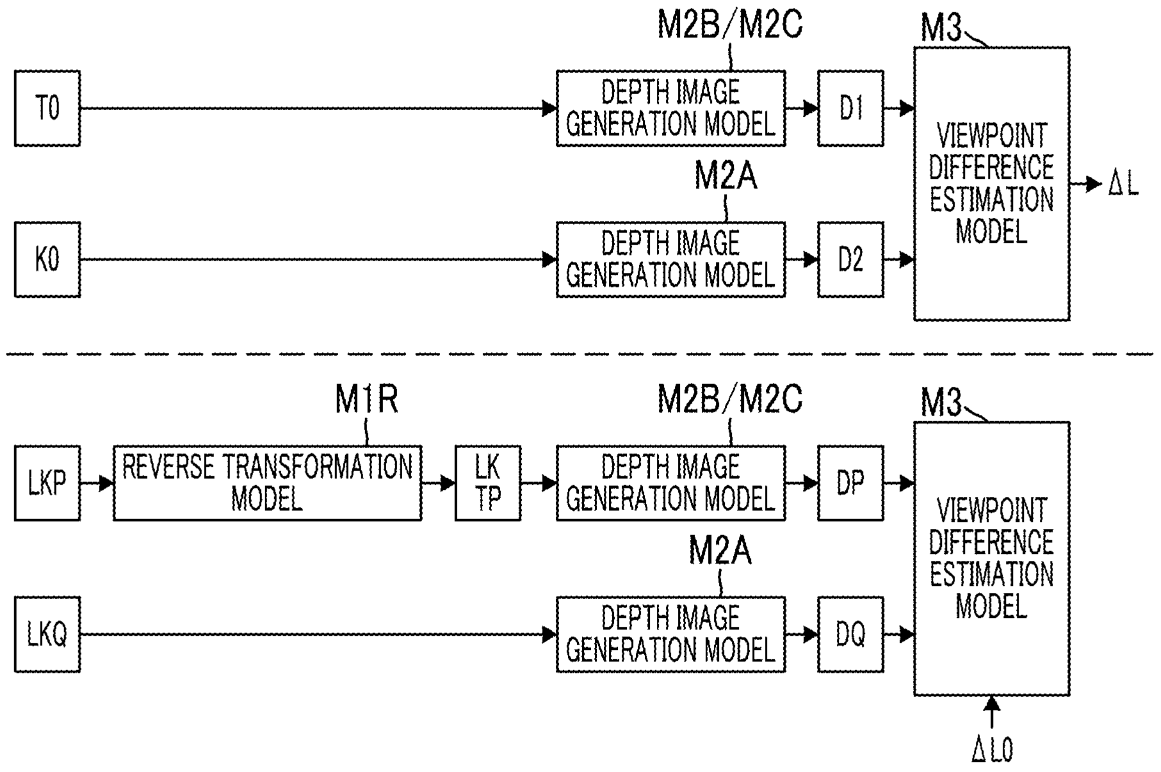
FIG. 17 is a diagram showing contents of viewpoint difference estimation processing according to Example 1-2.

FIG. 17 shows an overview of viewpoint difference estimation processing according to Example 1-2. In the training phase in the present example, the training unit 15 generates a virtual-to-real transformed image for training LKTP by inputting the virtual image for training LKP as viewed from the virtual viewpoint P1 to the reverse transformation model M1R. Further, the training unit 15 generates the depth image DP by inputting the virtual-to-real transformed image for training LKTP to the depth image generation model M2B or M2C. Further, the training unit 15 generates the depth image DQ by inputting the virtual image for training LKQ as viewed from the virtual viewpoint P2 to the depth image generation model M2A. In addition, the training unit 15 trains the viewpoint difference estimation model M3 by using, as training data, the viewpoint difference ΔL0 between the virtual viewpoint P1 and the virtual viewpoint P2, and the depth images DP and DQ.

In the operational phase in the present example, the generation unit 13 generates the first depth image D1 by inputting the real image T0 to the depth image generation model M2B or M2C. In addition, the generation unit 13 generates the second depth image D2 by inputting the virtual image K0 to the depth image generation model M2A. The estimation unit 14 estimates the viewpoint difference ΔL by inputting the first depth image D1 and the second depth image D2 to the viewpoint difference estimation model M3.

Example 1-3

Figure 18:
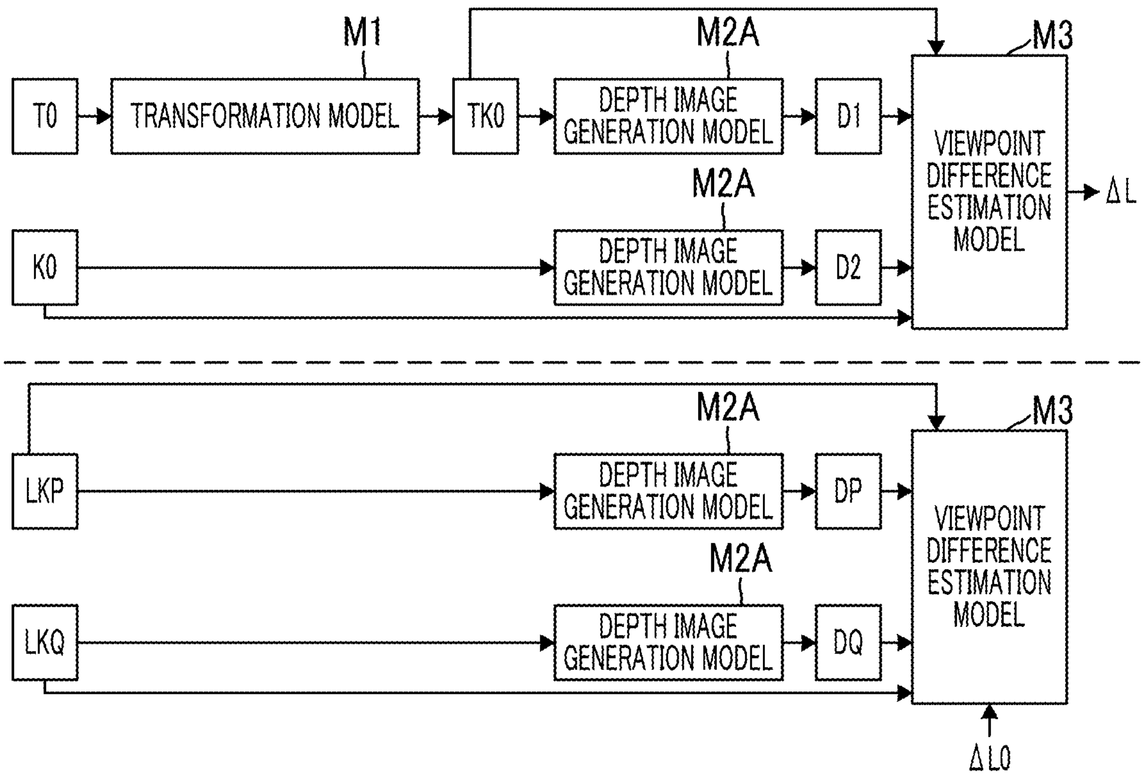
FIG. 18 is a diagram showing contents of viewpoint difference estimation processing according to Example 1-3.

FIG. 18 shows an overview of viewpoint difference estimation processing according to Example 1-3. In the training phase in the present example, the training unit 15 generates the depth image DP by inputting the virtual image for training LKP as viewed from the virtual viewpoint P1 to the depth image generation model M2A. Further, the training unit 15 generates the depth image DQ by inputting the virtual image for training LKQ as viewed from the virtual viewpoint P2 to the depth image generation model M2A. In addition, the training unit 15 trains the viewpoint difference estimation model M3 by using, as training data, the viewpoint difference ΔL0 between the virtual viewpoints P1 and P2, the depth images DP and DQ, and the virtual images for training LKP and LKQ.

In the operational phase in the present example, the transformation unit 12 transforms the real image T0 into the real-to-virtual transformed image TK0 by inputting the real image T0 to the transformation model M1. The generation unit 13 generates the first depth image D1 by inputting the real-to-virtual transformed image TK0 to the depth image generation model M2A. In addition, the generation unit 13 generates the second depth image D2 by inputting the virtual image K0 to the depth image generation model M2A. The estimation unit 14 estimates the viewpoint difference ΔL by inputting the first depth image D1, the second depth image D2, the real-to-virtual transformed image TK0, and the virtual image K0 to the viewpoint difference estimation model M3.

Example 1-4

Figure 19:
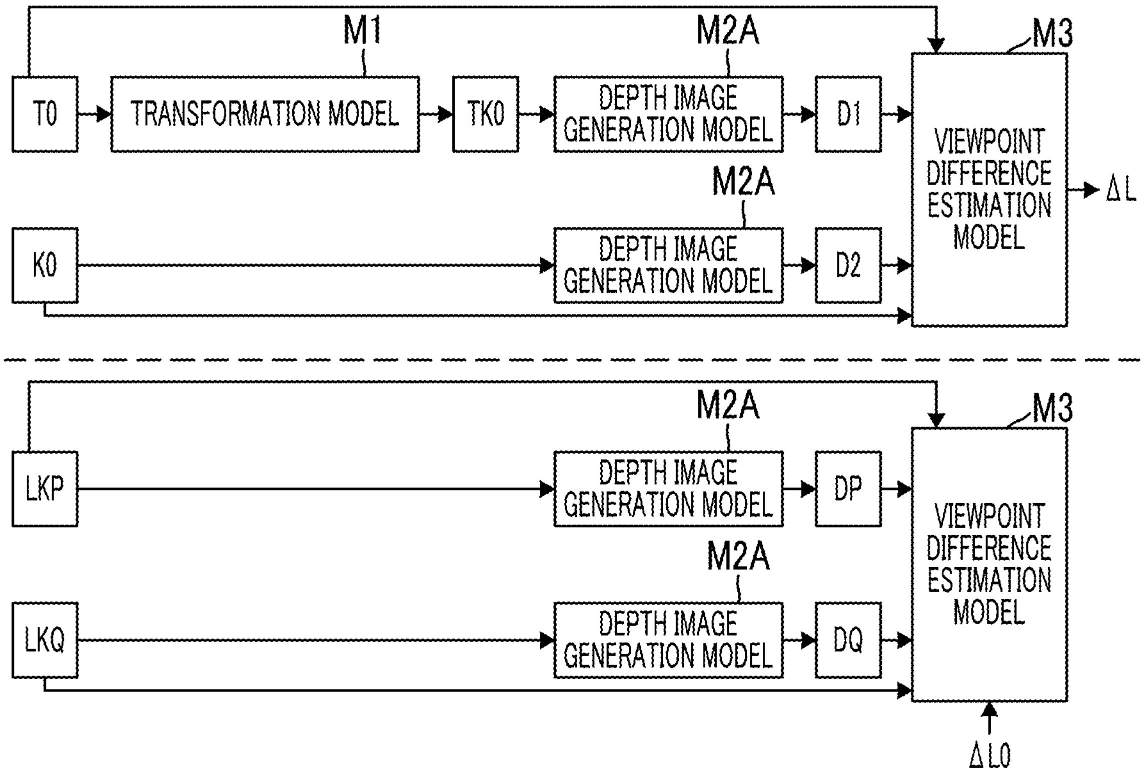
FIG. 19 is a diagram showing contents of viewpoint difference estimation processing according to Example 1-4.

FIG. 19 shows an overview of viewpoint difference estimation processing according to Example 1-4. In the training phase in the present example, the training unit 15 generates the depth image DP by inputting the virtual image for training LKP as viewed from the virtual viewpoint P1 to the depth image generation model M2A. Further, the training unit 15 generates the depth image DQ by inputting the virtual image for training LKQ as viewed from the virtual viewpoint P2 to the depth image generation model M2A. In addition, the training unit 15 trains the viewpoint difference estimation model M3 by using, as training data, the viewpoint difference ΔL0 between the virtual viewpoints P1 and P2, the depth images DP and DQ, and the virtual images for training LKP and LKQ.

In the operational phase in the present example, the transformation unit 12 transforms the real image T0 into the real-to-virtual transformed image TK0 by inputting the real image T0 to the transformation model ML. The generation unit 13 generates the first depth image D1 by inputting the real-to-virtual transformed image TK0 to the depth image generation model M2A. In addition, the generation unit 13 generates the second depth image D2 by inputting the virtual image K0 to the depth image generation model M2A. The estimation unit 14 estimates the viewpoint difference ΔL by inputting the first depth image D1, the second depth image D2, the real image T0, and the virtual image K0 to the viewpoint difference estimation model M3.

Next, description of Examples 2-1 to 2-5 will be made. In Examples, training is performed in the training phase by using two virtual images for training LKP and LKQ, and the viewpoint difference ΔL is estimated in the operational phase based on one depth image D1 or D2. In this case, there is an advantage that the ground truth data is accurate and easy to prepare. In Examples 2-1 to 2-5, the virtual image for training LKP is an example of a first virtual image for training according to the present disclosure, and the virtual image for training LKQ is an example of a second virtual image for training according to the present disclosure. In addition, the depth image DP is an example of a first depth image for training according to the present disclosure, and the depth image DQ is an example of a second depth image for training according to the present disclosure.

Example 2-1

Figure 20:
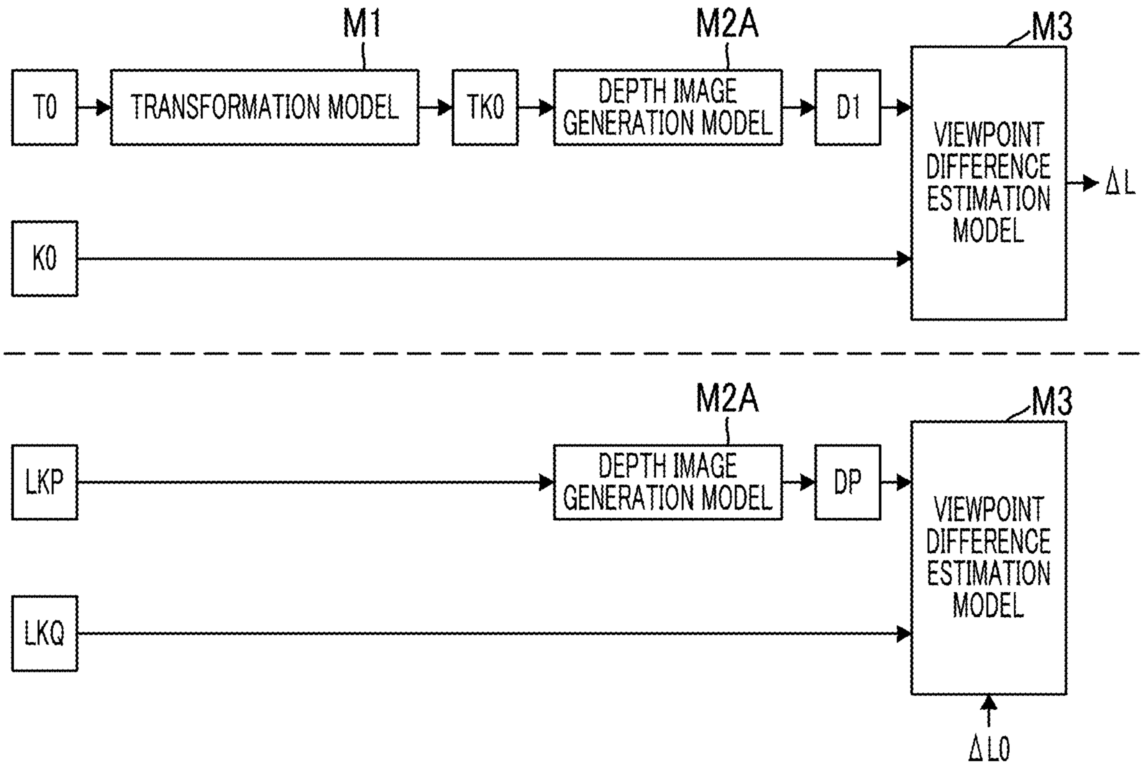
FIG. 20 is a diagram showing contents of viewpoint difference estimation processing according to Example 2-1.

FIG. 20 shows an overview of viewpoint difference estimation processing according to Example 2-1. In the training phase in the present example, the training unit 15 generates the depth image DP by inputting the virtual image for training LKP as viewed from the virtual viewpoint P1 to the depth image generation model M2A. In addition, the training unit 15 trains the viewpoint difference estimation model M3 by using, as training data, the virtual image for training LKQ as viewed from the virtual viewpoint P2, the viewpoint difference ΔL0 between the virtual viewpoint P1 and the virtual viewpoint P2, and the depth image DP.

In the operational phase in the present example, the transformation unit 12 transforms the real image T0 into the real-to-virtual transformed image TK0 by inputting the real image T0 to the transformation model M1. The generation unit 13 generates the first depth image D1 by inputting the real-to-virtual transformed image TK0 to the depth image generation model M2A. The estimation unit 14 estimates the viewpoint difference ΔL by inputting the first depth image D1 and the virtual image K0 to the viewpoint difference estimation model M3.

Example 2-2

Figure 21:
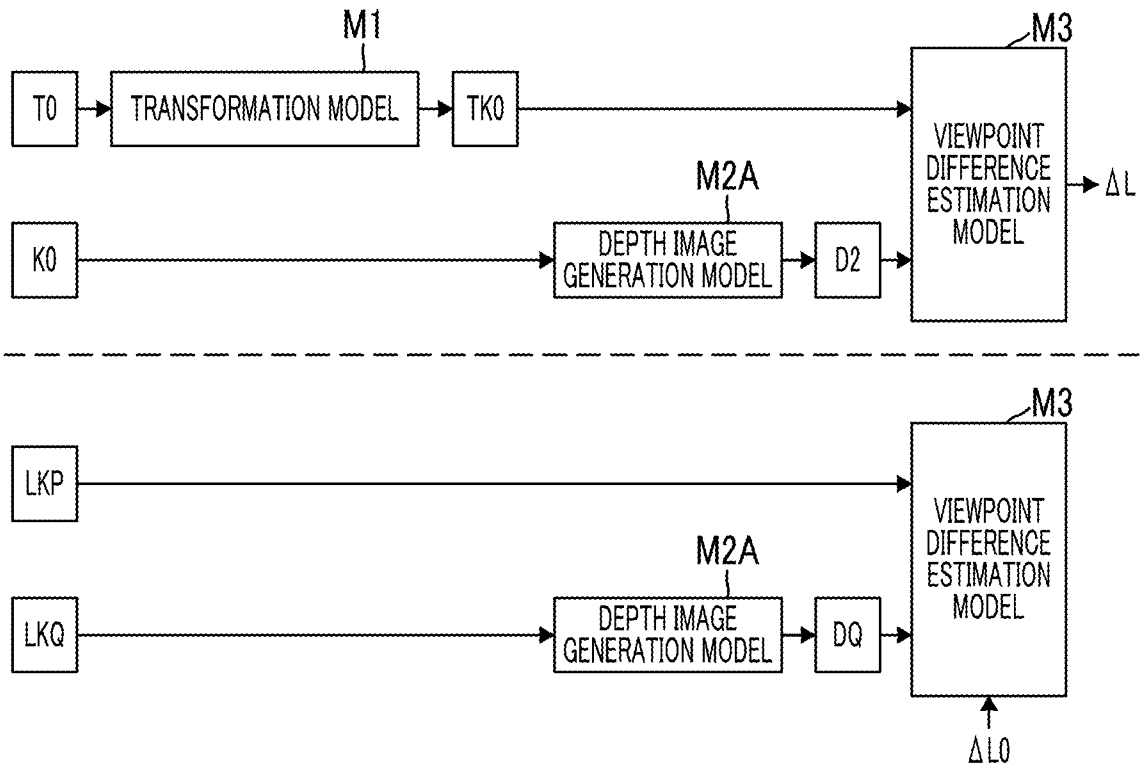
FIG. 21 is a diagram showing contents of viewpoint difference estimation processing according to Example 2-2.

FIG. 21 shows an overview of viewpoint difference estimation processing according to Example 2-2. In the training phase in the present example, the training unit 15 generates the depth image DQ by inputting the virtual image for training LKQ as viewed from the virtual viewpoint P2 to the depth image generation model M2A. In addition, the training unit 15 trains the viewpoint difference estimation model M3 by using, as training data, the virtual image for training LKP as viewed from the virtual viewpoint P1, the viewpoint difference ΔL0 between the virtual viewpoint P1 and the virtual viewpoint P2, and the depth image DQ.

In the operational phase in the present example, the transformation unit 12 transforms the real image T0 into the real-to-virtual transformed image TK0 by inputting the real image T0 to the transformation model ML. The generation unit 13 generates the second depth image D2 by inputting the virtual image K0 to the depth image generation model M2A. The estimation unit 14 estimates the viewpoint difference ΔL by inputting the real-to-virtual transformed image TK0 and the second depth image D2 to the viewpoint difference estimation model M3.

Example 2-3

Figure 22:
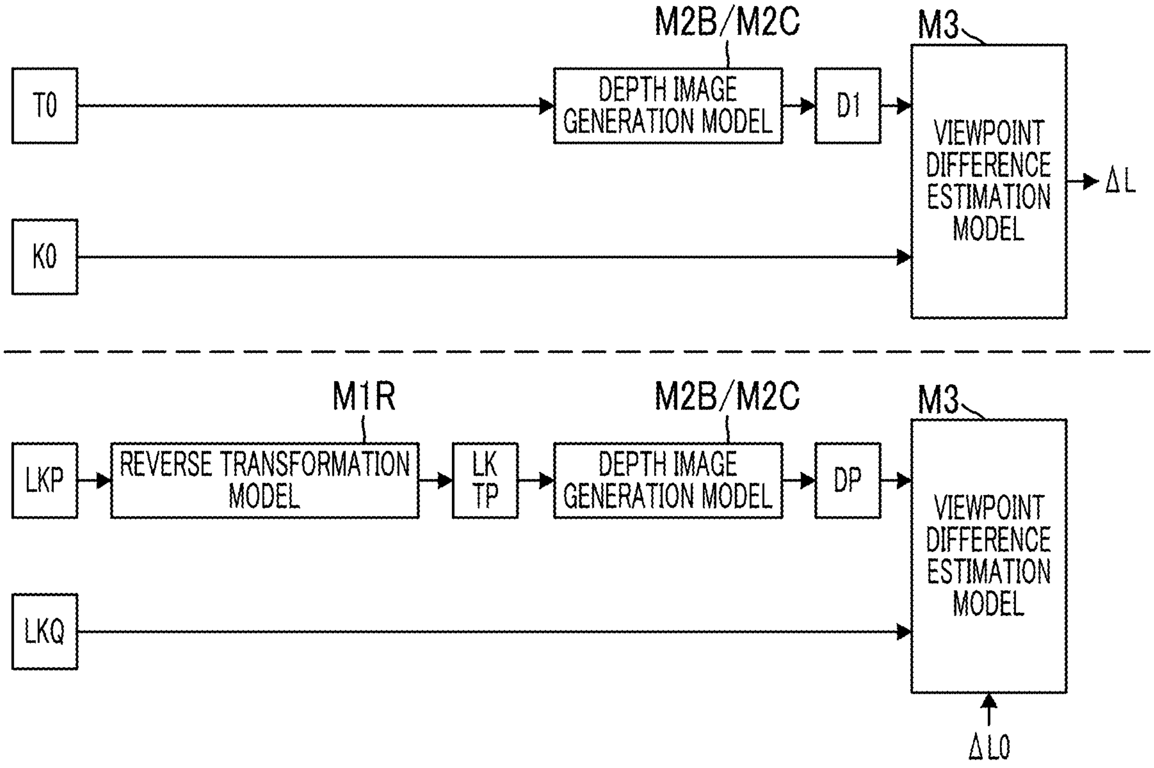
FIG. 22 is a diagram showing contents of viewpoint difference estimation processing according to Example 2-3.

FIG. 22 shows an overview of viewpoint difference estimation processing according to Example 2-3. In the training phase in the present example, the training unit 15 generates a virtual-to-real transformed image for training LKTP by inputting the virtual image for training LKP as viewed from the virtual viewpoint P1 to the reverse transformation model M1R. Further, the training unit 15 generates the depth image DP by inputting the virtual-to-real transformed image for training LKTP to the depth image generation model M2B or M2C. In addition, the training unit 15 trains the viewpoint difference estimation model M3 by using, as training data, the virtual image for training LKQ as viewed from the virtual viewpoint P2, the viewpoint difference ΔL0 between the virtual viewpoint P1 and the virtual viewpoint P2, the depth image DP, and the virtual image for training LKQ.

In the operational phase in the present example, the generation unit 13 generates the first depth image D1 by inputting the real image T0 to the depth image generation model M2B or M2C. That is, the first depth image D1 may be generated based on the pixel value of the real image T0. The estimation unit 14 estimates the viewpoint difference ΔL by inputting the first depth image D1 and the virtual image K0 to the viewpoint difference estimation model M3.

Example 2-4

Figure 23:
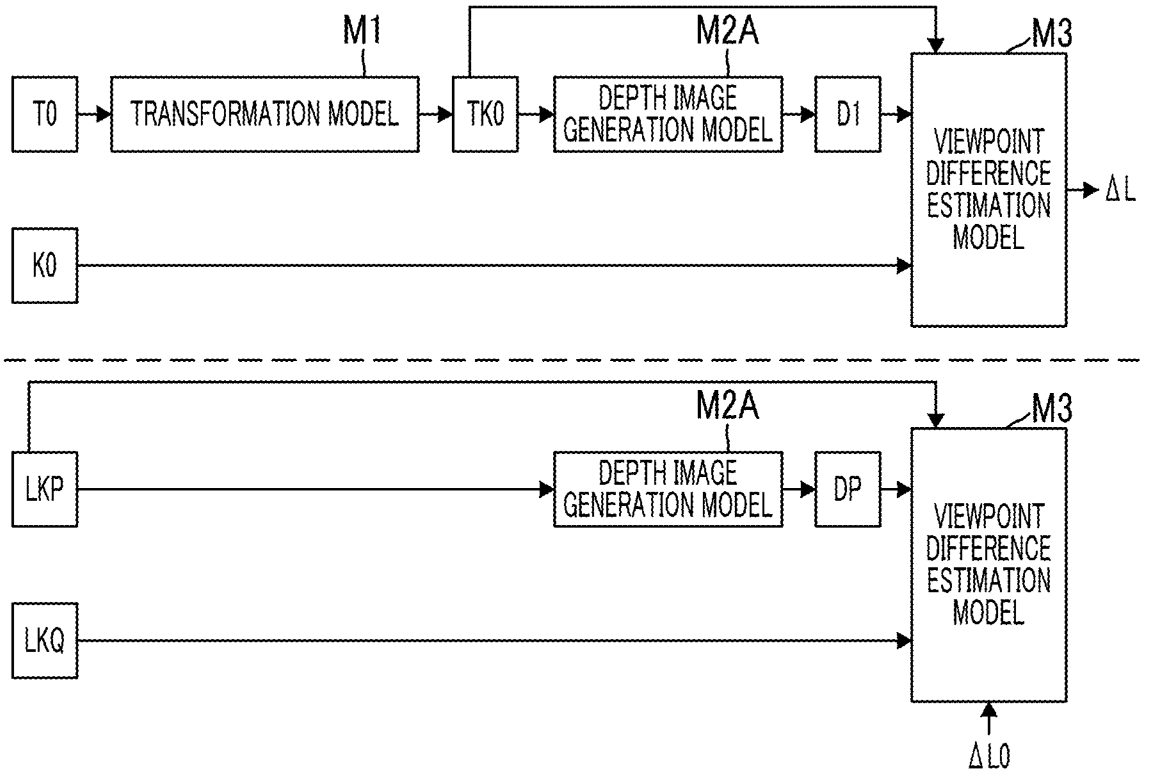
FIG. 23 is a diagram showing contents of viewpoint difference estimation processing according to Example 2-4.

FIG. 23 shows an overview of viewpoint difference estimation processing according to Example 2-4. In the training phase in the present example, the training unit 15 generates the depth image DP by inputting the virtual image for training LKP as viewed from the virtual viewpoint P1 to the depth image generation model M2A. In addition, the training unit 15 trains the viewpoint difference estimation model M3 by using, as training data, the virtual image for training LKP, the virtual image for training LKQ as viewed from the virtual viewpoint P2, the viewpoint difference ΔL0 between the virtual viewpoint P1 and the virtual viewpoint P2, and the depth image DP.

In the operational phase in the present example, the transformation unit 12 transforms the real image T0 into the real-to-virtual transformed image TK0 by inputting the real image T0 to the transformation model ML. The generation unit 13 generates the first depth image D1 by inputting the real-to-virtual transformed image TK0 to the depth image generation model M2A. The estimation unit 14 estimates the viewpoint difference ΔL by inputting the first depth image D1, the real-to-virtual transformed image TK0, and the virtual image K0 to the viewpoint difference estimation model M3.

Example 2-5

Figure 24:
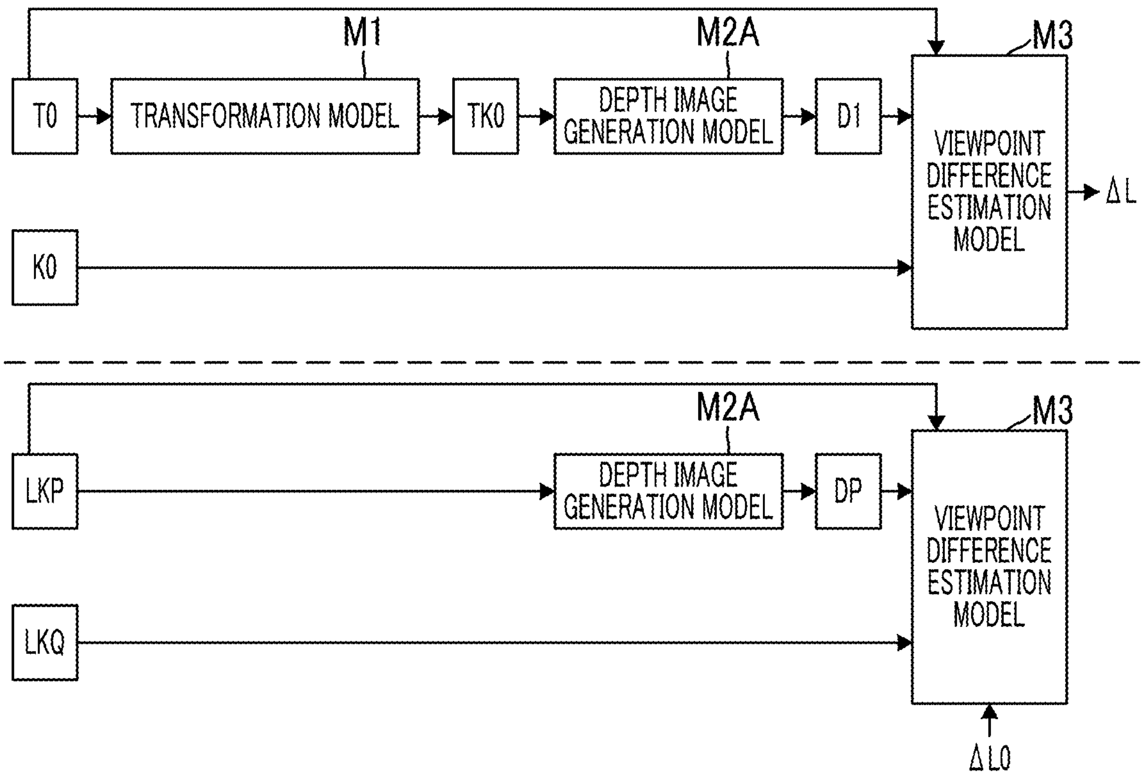
FIG. 24 is a diagram showing contents of viewpoint difference estimation processing according to Example 2-5.

FIG. 24 shows an overview of viewpoint difference estimation processing according to Example 2-5. In the training phase in the present example, the training unit 15 generates the depth image DP by inputting the virtual image for training LKP as viewed from the virtual viewpoint P1 to the depth image generation model M2A. In addition, the training unit 15 trains the viewpoint difference estimation model M3 by using, as training data, the virtual image for training LKP, the virtual image for training LKQ as viewed from the virtual viewpoint P2, the viewpoint difference ΔL0 between the virtual viewpoint P1 and the virtual viewpoint P2, and the depth image DP.

In the operational phase in the present example, the transformation unit 12 transforms the real image T0 into the real-to-virtual transformed image TK0 by inputting the real image T0 to the transformation model M1. The generation unit 13 generates the first depth image D1 by inputting the real-to-virtual transformed image TK0 to the depth image generation model M2A. The estimation unit 14 estimates the viewpoint difference ΔL by inputting the first depth image D1, the real image T0, and the virtual image K0 to the viewpoint difference estimation model M3.

Next, description of Example 3-1 to 3-3 will be made. In Examples, training is performed in the training phase by using one virtual image for training LK0 and one real image for training LT0, and the viewpoint difference ΔL is estimated in the operational phase based on two depth images D1 and D2. Since training is performed by using the same real image for training LT0 as the input (real image T0) in the operational phase, it is difficult to prepare the training data, but the accuracy of the viewpoint difference estimation is improved. In Examples 3-1 to 3-3, the depth image Dt0 is an example of a depth image for training according to the present disclosure, and the depth image Dk0 is an example of a virtual depth image for training according to the present disclosure.

Example 3-1

Figure 25:
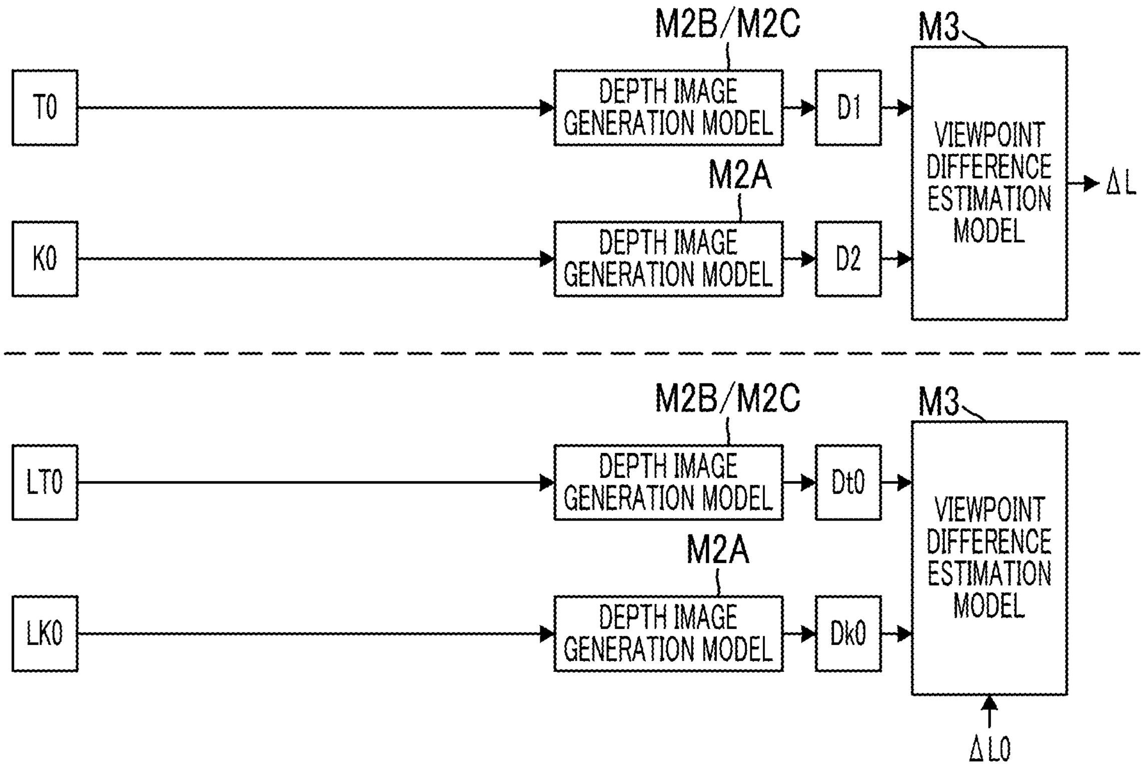
FIG. 25 is a diagram showing contents of viewpoint difference estimation processing according to Example 3-1.

FIG. 25 shows an overview of viewpoint difference estimation processing according to Example 3-1. In the training phase in the present example, the training unit 15 generates the depth image Dt0 by inputting the real image for training LT0 to the depth image generation model M2B or M2C. Further, the training unit 15 generates the depth image Dk0 by inputting the virtual image for training LK0 as viewed from the virtual viewpoint P3 to the depth image generation model M2A. In addition, the training unit 15 trains the viewpoint difference estimation model M3 by using, as training data, the viewpoint difference ΔL0 between the viewpoint of the real image for training LT0 and the virtual viewpoint P3, and the depth images Dt0 and Dk0.

In the operational phase in the present example, the generation unit 13 generates the first depth image D1 by inputting the real image T0 to the depth image generation model M2B or M2C. In addition, the generation unit 13 generates the second depth image D2 by inputting the virtual image K0 to the depth image generation model M2A. The estimation unit 14 estimates the viewpoint difference ΔL by inputting the first depth image D1 and the second depth image D2 to the viewpoint difference estimation model M3.

Example 3-2

Figure 26:
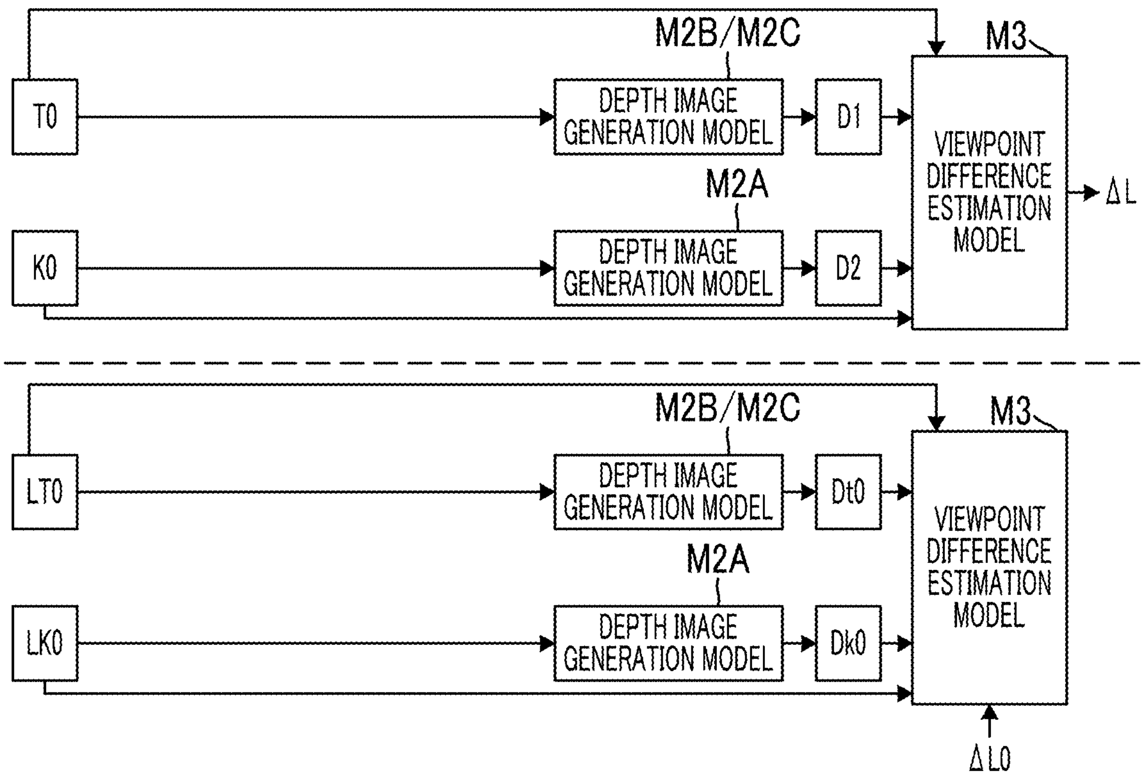
FIG. 26 is a diagram showing contents of viewpoint difference estimation processing according to Example 3-2.

FIG. 26 shows an overview of viewpoint difference estimation processing according to Example 3-2. In the training phase in the present example, the training unit 15 generates the depth image Dt0 by inputting the real image for training LT0 to the depth image generation model M2B or M2C. Further, the training unit 15 generates the depth image Dk0 by inputting the virtual image for training LK0 as viewed from the virtual viewpoint P3 to the depth image generation model M2A. In addition, the training unit 15 trains the viewpoint difference estimation model M3 by using, as training data, the viewpoint difference ΔL0 between the viewpoint of the real image for training LT0 and the virtual viewpoint P3, the depth images Dt0 and Dk0, the real image for training LT0, and the virtual image for training LK0.

In the operational phase in the present example, the generation unit 13 generates the first depth image D1 by inputting the real image T0 to the depth image generation model M2B or M2C. In addition, the generation unit 13 generates the second depth image D2 by inputting the virtual image K0 to the depth image generation model M2A. The estimation unit 14 estimates the viewpoint difference ΔL by inputting the first depth image D1, the second depth image D2, the real image T0, and the virtual image K0 to the viewpoint difference estimation model M3.

Example 3-3

Figure 27:
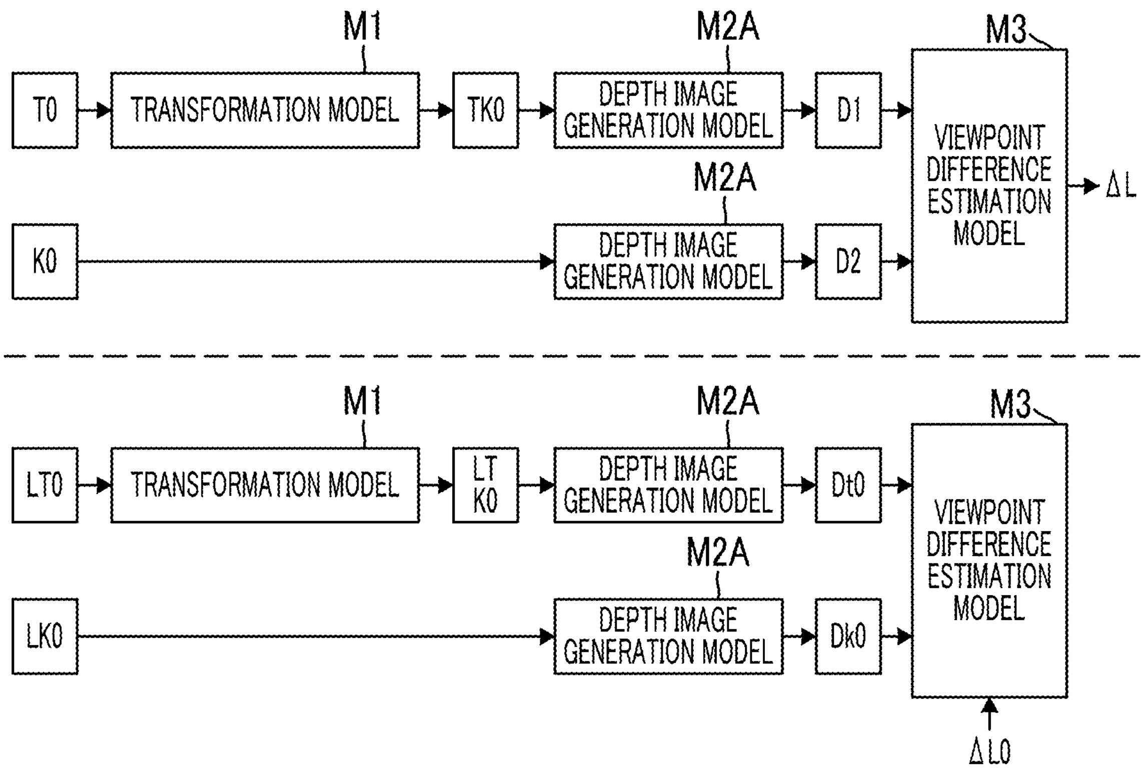
FIG. 27 is a diagram showing contents of viewpoint difference estimation processing according to Example 3-3.

FIG. 27 shows an overview of viewpoint difference estimation processing according to Example 3-3. In the training phase in the present example, the training unit 15 transforms the real image for training LT0 into the real-to-virtual transformed image for training LTK0 by inputting the real image for training LT0 to the transformation model M1. Further, the training unit 15 generates the depth image Dt0 by inputting the real-to-virtual transformed image for training LTK0 to the depth image generation model M2A. Further, the training unit 15 generates the depth image Dk0 by inputting the virtual image for training LK0 as viewed from the virtual viewpoint P3 to the depth image generation model M2A. In addition, the training unit 15 trains the viewpoint difference estimation model M3 by using, as training data, the viewpoint difference ΔL0 between the viewpoint of the real image for training LT0 and the virtual viewpoint P3, and the depth images Dt0 and Dk0.

In the operational phase in the present example, the generation unit 13 transforms the real image T0 into the real-to-virtual transformed image TK0 by inputting the real image T0 to the transformation model M1. In addition, the generation unit 13 generates the first depth image D1 by inputting the real-to-virtual transformed image TK0 to the depth image generation model M2A. In addition, the generation unit 13 generates the second depth image D2 by inputting the virtual image K0 to the depth image generation model M2A. The estimation unit 14 estimates the viewpoint difference ΔL by inputting the first depth image D1, the second depth image D2, the real image T0, and the virtual image K0 to the viewpoint difference estimation model M3.

First, description of Examples 4-1 to 4-4 will be made. In Examples, training is performed in the training phase by using one virtual image for training LK0 and one real image for training LT0, and the viewpoint difference ΔL is estimated in the operational phase based on one depth image D1 or D2. Since training is performed by using the same real image for training LT0 as the input (real image T0) in the operational phase, it is difficult to prepare the training data, but the accuracy of the viewpoint difference estimation is improved. In Examples 4-1 to 4-4, the depth image Dt0 is an example of a depth image for training according to the present disclosure, and the depth image Dk0 is an example of a virtual depth image for training according to the present disclosure.

Example 4-1

Figure 28:
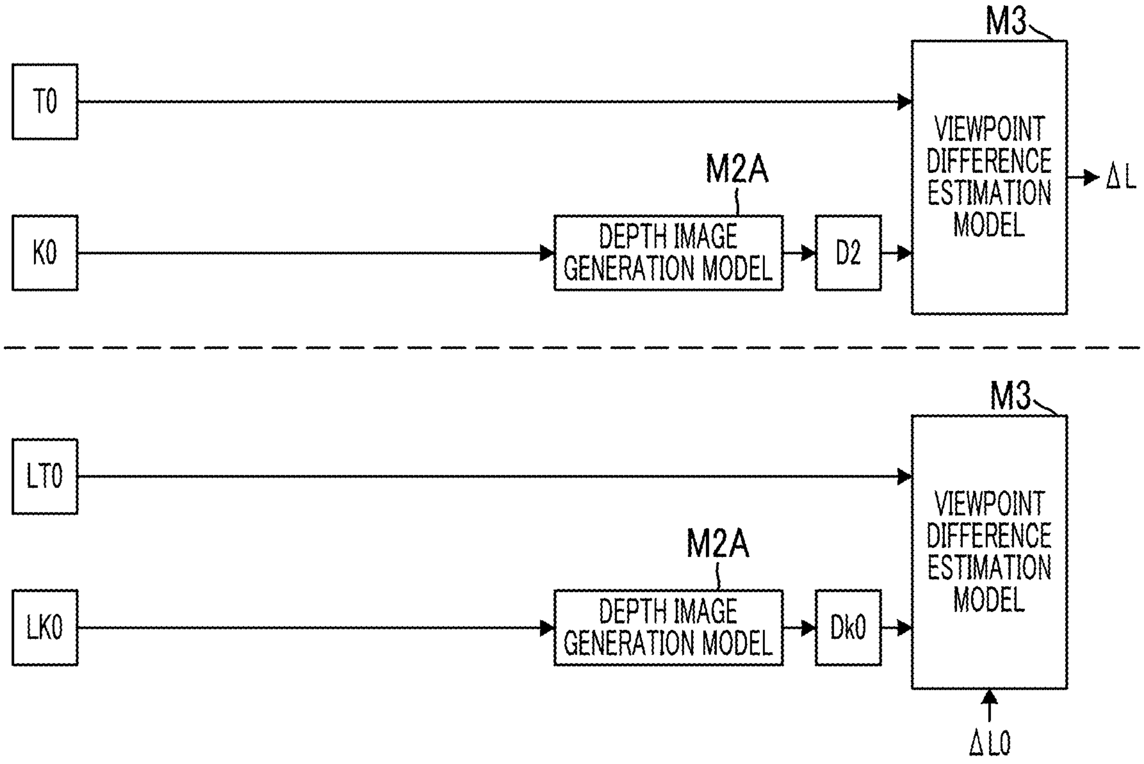
FIG. 28 is a diagram showing contents of viewpoint difference estimation processing according to Example 4-1.

FIG. 28 shows an overview of viewpoint difference estimation processing according to Example 4-1. In the training phase in the present example, the training unit 15 generates the depth image Dk0 by inputting the virtual image for training LK0 as viewed from the virtual viewpoint P3 to the depth image generation model M2A. In addition, the training unit 15 trains the viewpoint difference estimation model M3 by using, as training data, the viewpoint difference ΔL0 between the viewpoint of the real image for training LT0 and the virtual viewpoint P3, the depth image Dk0, and the real image for training LT0.

In the operational phase in the present example, the generation unit 13 generates the second depth image D2 by inputting the virtual image K0 to the depth image generation model M2A. The estimation unit 14 estimates the viewpoint difference ΔL by inputting the second depth image D2 and the real image T0 to the viewpoint difference estimation model M3.

Example 4-2

Figure 29:
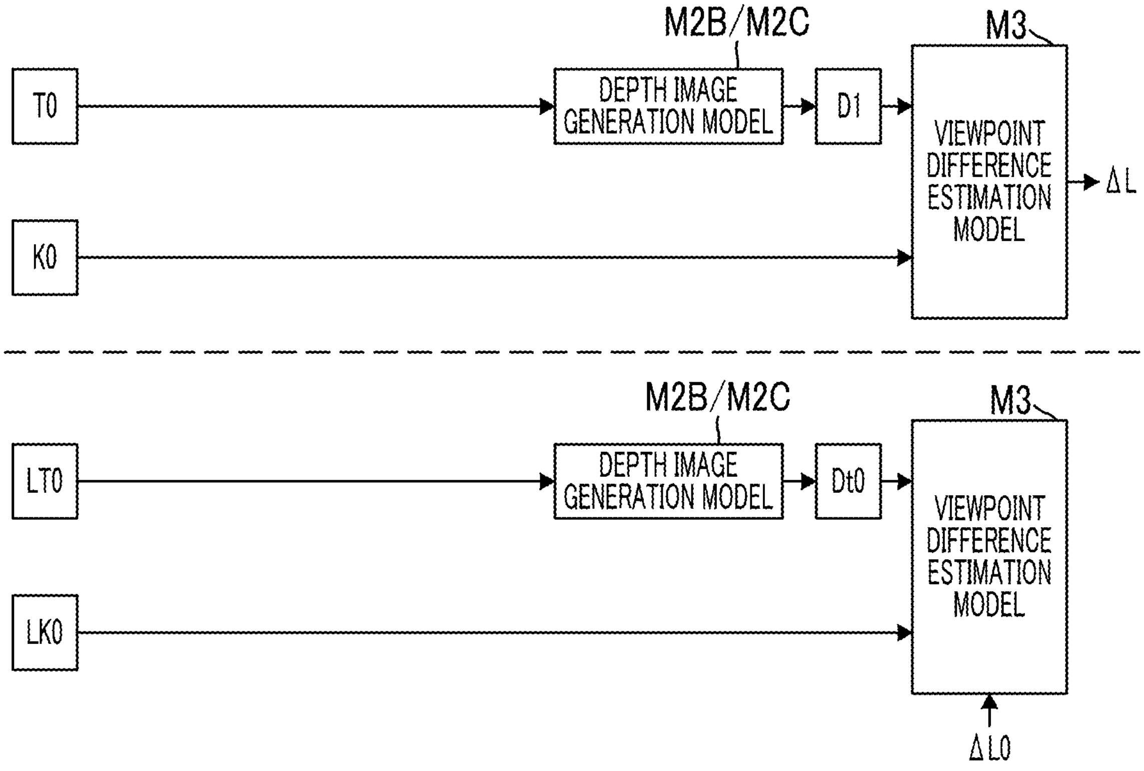
FIG. 29 is a diagram showing contents of viewpoint difference estimation processing according to Example 4-2.

FIG. 29 shows an overview of viewpoint difference estimation processing according to Example 4-2. In the training phase in the present example, the training unit 15 generates the depth image Dt0 by inputting the real image for training LT0 to the depth image generation model M2B or M2C. In addition, the training unit 15 trains the viewpoint difference estimation model M3 by using, as training data, the virtual image for training LK0 as viewed from the virtual viewpoint P3, the viewpoint difference ΔL0 between the viewpoint of the real image for training LT0 and the virtual viewpoint P3, and the depth image Dt0.

In the operational phase in the present example, the generation unit 13 generates the first depth image D1 by inputting the real image T0 to the depth image generation model M2B or M2C. The estimation unit 14 estimates the viewpoint difference ΔL by inputting the first depth image D1 and the virtual image K0 to the viewpoint difference estimation model M3.

Example 4-3

Figure 30:
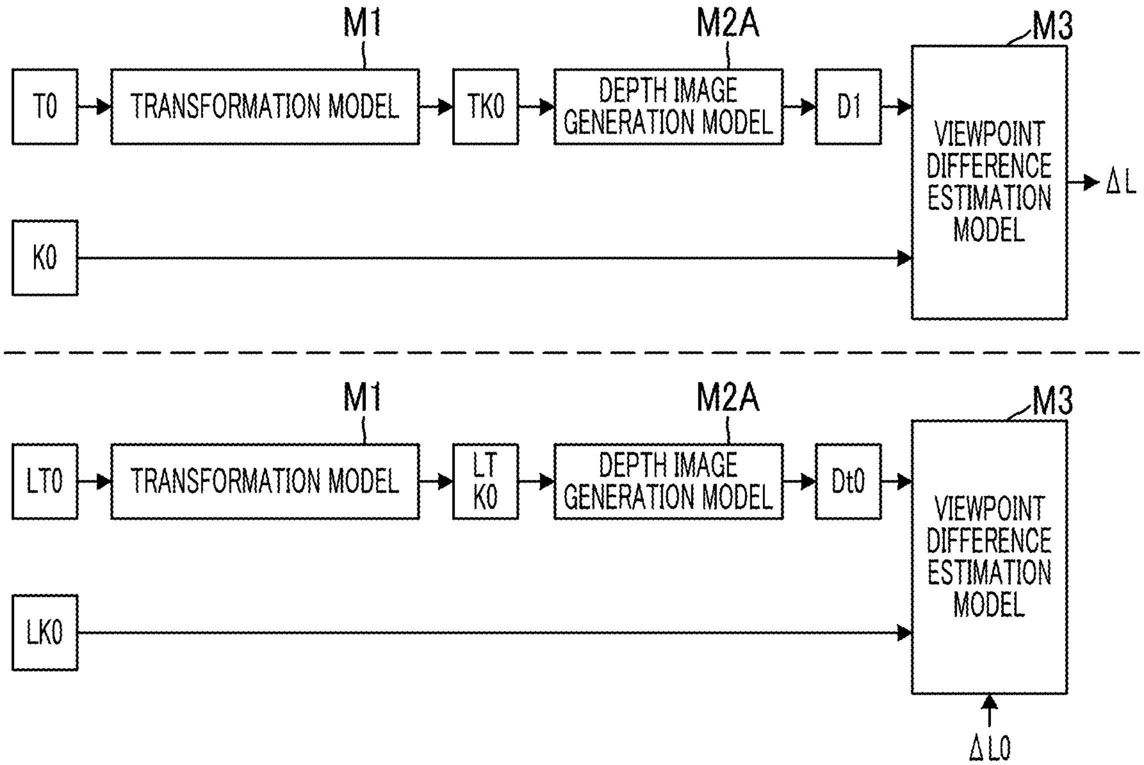
FIG. 30 is a diagram showing contents of viewpoint difference estimation processing according to Example 4-3.

FIG. 30 shows an overview of viewpoint difference estimation processing according to Example 4-3. In the training phase in the present example, the training unit 15 transforms the real image for training LT0 into the real-to-virtual transformed image for training LTK0 by inputting the real image for training LT0 to the transformation model M1. Further, the training unit 15 generates the depth image Dt0 by inputting the real-to-virtual transformed image for training LTK0 to the depth image generation model M2A. In addition, the training unit 15 trains the viewpoint difference estimation model M3 by using, as training data, the virtual image for training LK0 as viewed from the virtual viewpoint P3, the viewpoint difference ΔL0 between the viewpoint of the real image for training LT0 and the virtual viewpoint P3, and the depth image Dt0.

In the operational phase in the present example, the transformation unit 12 transforms the real image T0 into the real-to-virtual transformed image TK0 by inputting the real image T0 to the transformation model M1. The generation unit 13 generates the first depth image D1 by inputting the real-to-virtual transformed image TK0 to the depth image generation model M2A. The estimation unit 14 estimates the viewpoint difference ΔL by inputting the first depth image D1 and the virtual image K0 to the viewpoint difference estimation model M3.

Example 4-4

Figure 31:
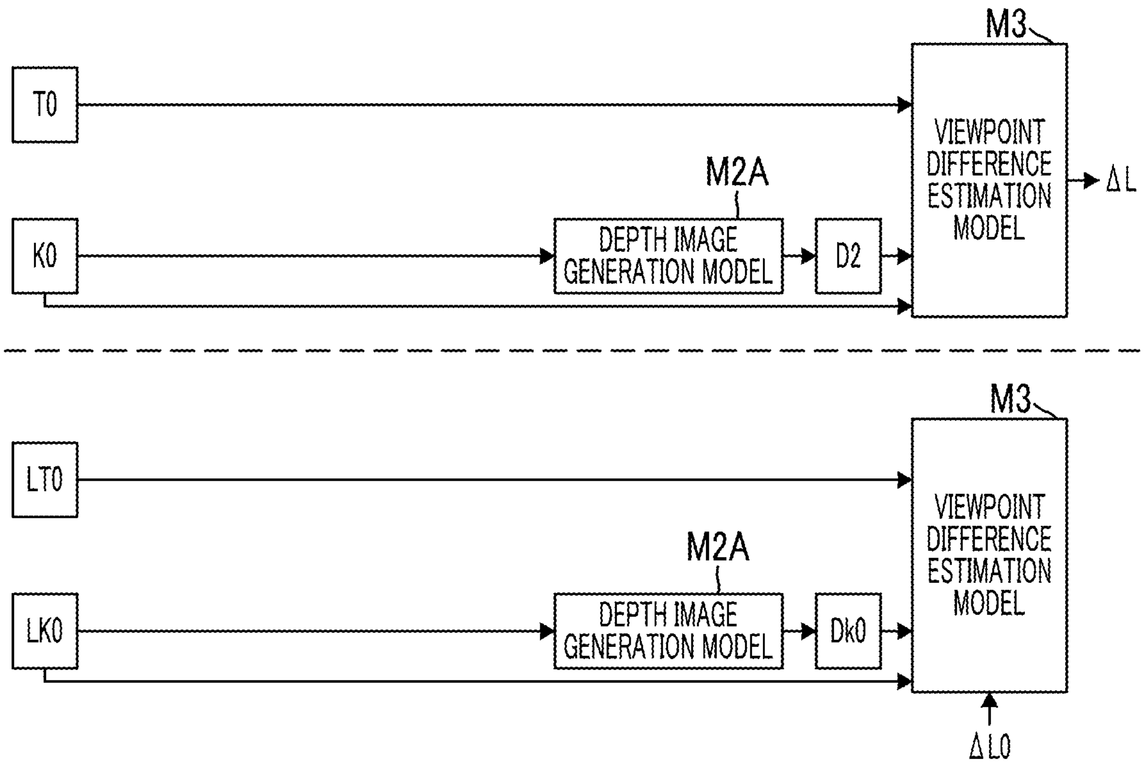
FIG. 31 is a diagram showing contents of viewpoint difference estimation processing according to Example 4-4.

FIG. 31 shows an overview of viewpoint difference estimation processing according to Example 4-4. In the training phase in the present example, the training unit 15 generates the depth image Dk0 by inputting the virtual image for training LK0 as viewed from the virtual viewpoint P3 to the depth image generation model M2A. In addition, the training unit 15 trains the viewpoint difference estimation model M3 by using, as training data, the viewpoint difference ΔL0 between the viewpoint of the real image for training LT0 and the virtual viewpoint P3, the depth image Dk0, and the real image for training LT0.

In the operational phase in the present example, the generation unit 13 generates the second depth image D2 by inputting the virtual image K0 to the depth image generation model M2A. The estimation unit 14 estimates the viewpoint difference ΔL by inputting the second depth image D2, the real image T0, and the virtual image K0 to the viewpoint difference estimation model M3.

Next, description of Example 5-1 to 5-3 will be made. In Examples, training is performed in the training phase by using two real images for training LTP and LTQ, and the viewpoint difference ΔL is estimated in the operational phase based on two depth images D1 and D2.

Example 5-1

Figure 32:
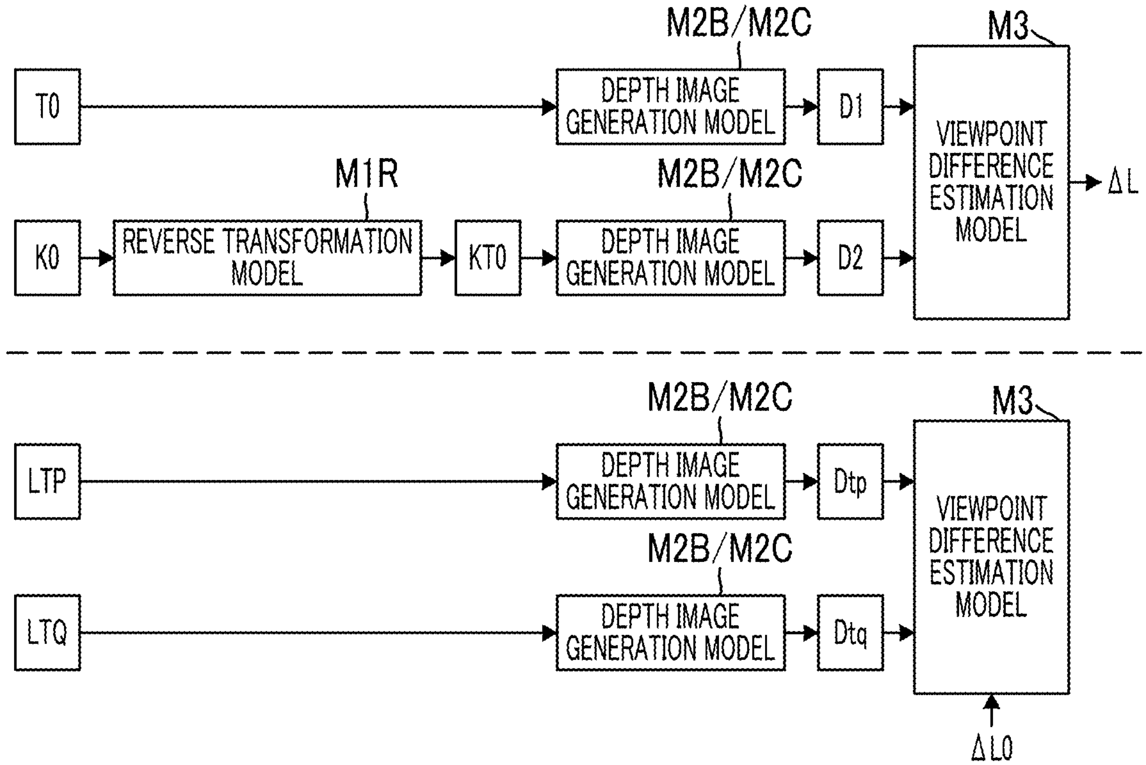
FIG. 32 is a diagram showing contents of viewpoint difference estimation processing according to Example 5-1.

FIG. 32 shows an overview of viewpoint difference estimation processing according to Example 5-1. In the training phase in the present example, the training unit 15 generates a depth image Dtp by inputting the real image for training LTP to the depth image generation model M2B or M2C. Further, the training unit 15 generates a depth image Dtq by inputting the real image for training LTQ to the depth image generation model M2B or M2C. In addition, the training unit 15 trains the viewpoint difference estimation model M3 by using, as training data, the viewpoint difference ΔL0 between the real images for training LTP and LKQ and the depth images Dtp and Dtq.

In the operational phase in the present example, the generation unit 13 generates the first depth image D1 by inputting the real image T0 to the depth image generation model M2B or M2C. The transformation unit 12 transforms the virtual image K0 into the virtual-to-real transformed image KT0 by inputting the virtual image K0 to the reverse transformation model M1R. In addition, the generation unit 13 generates the second depth image D2 by inputting the virtual-to-real transformed image KT0 to the depth image generation model M2B or M2C. The estimation unit 14 estimates the viewpoint difference ΔL by inputting the first depth image D1 and the second depth image D2 to the viewpoint difference estimation model M3.

Example 5-2

Figure 33:
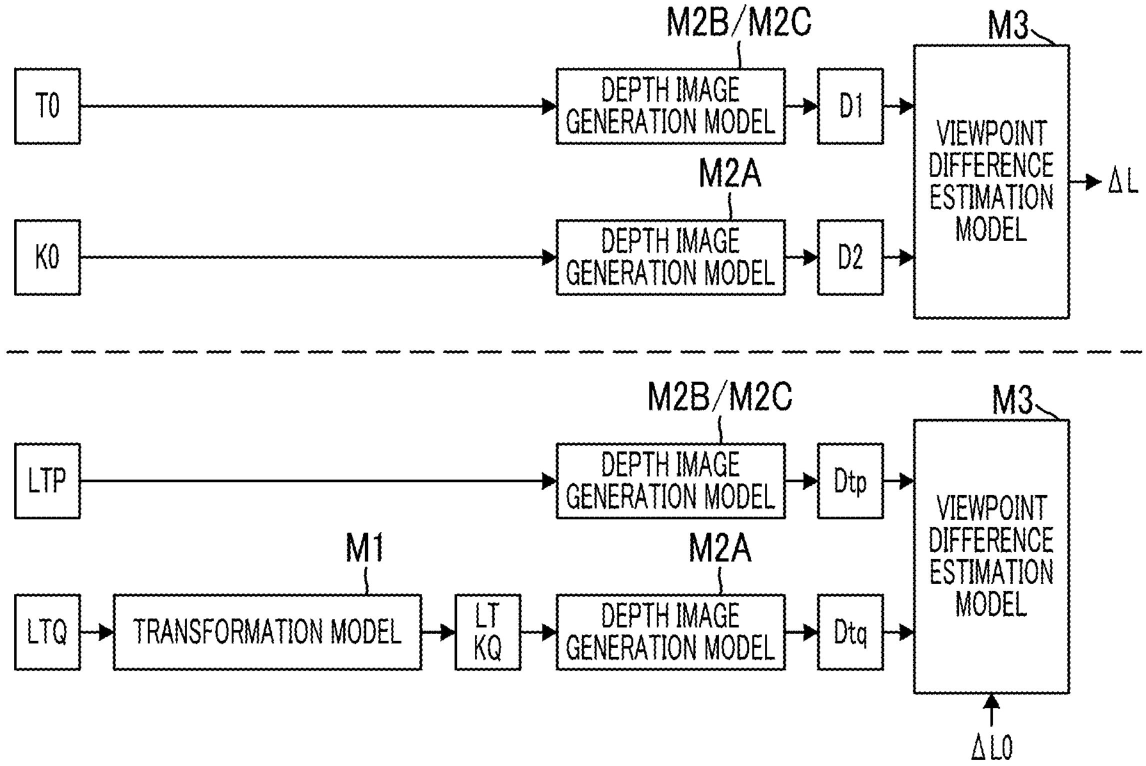
FIG. 33 is a diagram showing contents of viewpoint difference estimation processing according to Example 5-2.

FIG. 33 shows an overview of viewpoint difference estimation processing according to Example 5-2. In the training phase in the present example, the training unit 15 generates a depth image Dtp by inputting the real image for training LTP to the depth image generation model M2B or M2C. Further, the training unit 15 generates a real-to-virtual transformed image for training LTKQ by inputting the real image for training LTQ to the transformation model M1. Further, the training unit 15 generates the depth image Dtq by inputting the real-to-virtual transformed image for training LTKQ to the depth image generation model M2A. In addition, the training unit 15 trains the viewpoint difference estimation model M3 by using, as training data, the viewpoint difference ΔL0 between the real images for training LTP and LKQ and the depth images Dtp and Dtq.

In the operational phase in the present example, the generation unit 13 generates the first depth image D1 by inputting the real image T0 to the depth image generation model M2B or M2C. In addition, the generation unit 13 generates the second depth image D2 by inputting the virtual image K0 to the depth image generation model M2A. The estimation unit 14 estimates the viewpoint difference ΔL by inputting the first depth image D1 and the second depth image D2 to the viewpoint difference estimation model M3.

Example 5-3

Figure 34:
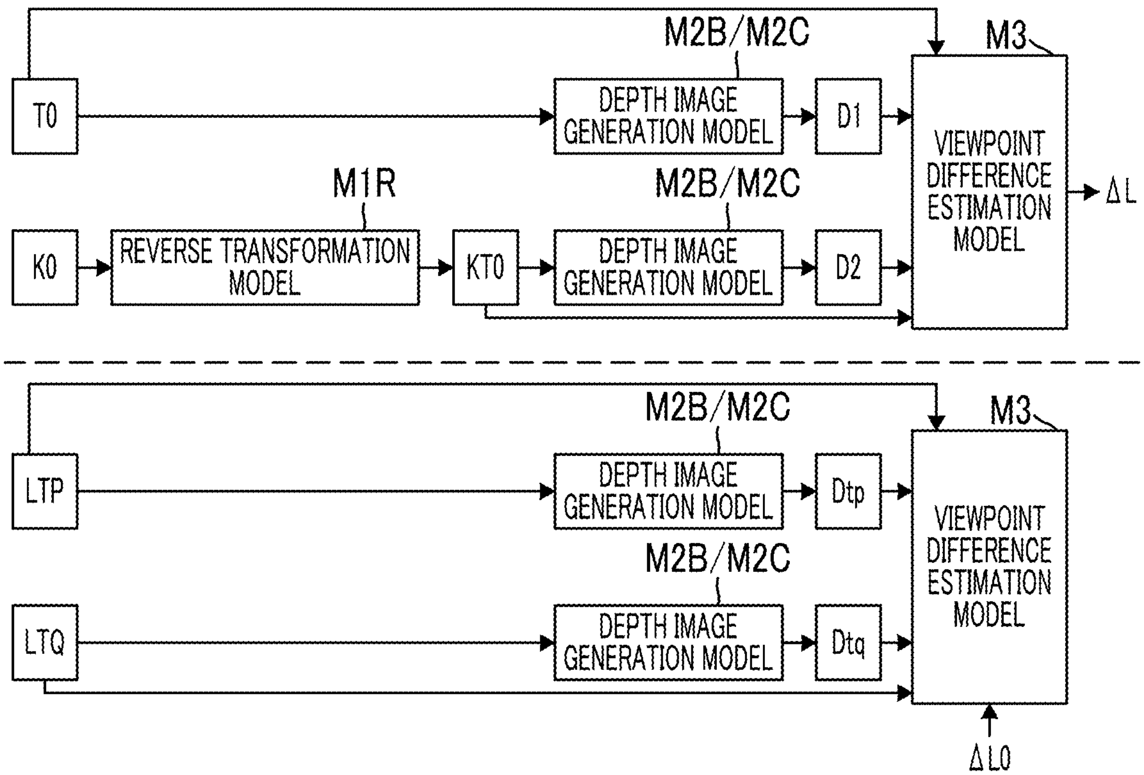
FIG. 34 is a diagram showing contents of viewpoint difference estimation processing according to Example 5-3.

FIG. 34 shows an overview of viewpoint difference estimation processing according to Example 5-3. In the training phase in the present example, the training unit 15 generates a depth image Dtp by inputting the real image for training LTP to the depth image generation model M2B or M2C. Further, the training unit 15 generates a depth image Dtq by inputting the real image for training LTQ to the depth image generation model M2B or M2C. In addition, the training unit 15 trains the viewpoint difference estimation model M3 by using, as training data, the viewpoint difference ΔL0 between the real images for training LTP and LKQ, the depth images Dtp and Dtq, and the real images for training LTP and LKQ.

In the operational phase in the present example, the generation unit 13 generates the first depth image D1 by inputting the real image T0 to the depth image generation model M2B or M2C. The transformation unit 12 transforms the virtual image K0 into the virtual-to-real transformed image KT0 by inputting the virtual image K0 to the reverse transformation model M1R. In addition, the generation unit 13 generates the second depth image D2 by inputting the virtual-to-real transformed image KT0 to the depth image generation model M2B or M2C. The estimation unit 14 estimates the viewpoint difference ΔL by inputting the first depth image D1, the second depth image D2, the real image T0, and the virtual-to-real transformed image KT0 to the viewpoint difference estimation model M3.

Next, description of Examples 6-1 to 6-2 will be made. In Examples, training is performed in the training phase by using two real images for training LTP and LTQ, and the viewpoint difference ΔL is estimated in the operational phase based on one depth image.

Example 6-1

Figure 35:
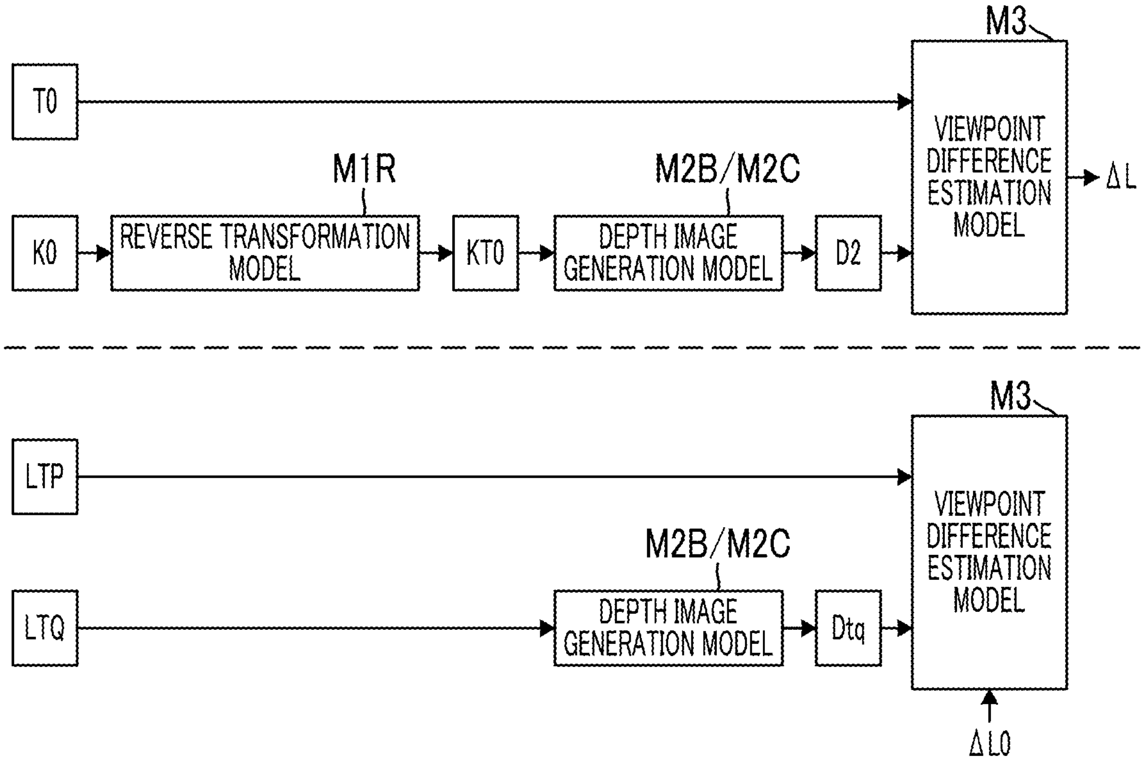
FIG. 35 is a diagram showing contents of viewpoint difference estimation processing according to Example 6-1.

FIG. 35 shows an overview of viewpoint difference estimation processing according to Example 6-1. In the training phase in the present example, the training unit 15 generates the depth image LDQ by inputting the real image for training LTQ to the depth image generation model M2B or M2C. In addition, the training unit 15 trains the viewpoint difference estimation model M3 by using, as training data, the viewpoint difference ΔL0 between the real images for training LTP and LKQ, the depth image LDQ, and the real image for training LTP.

In the operational phase in the present example, the transformation unit 12 transforms the virtual image K0 into the virtual-to-real transformed image KT0 by inputting the virtual image K0 to the reverse transformation model M1R. In addition, the generation unit 13 generates the second depth image D2 by inputting the virtual-to-real transformed image KT0 to the depth image generation model M2B or M2C. The estimation unit 14 estimates the viewpoint difference ΔL by inputting the second depth image D2 and the real image T0 to the viewpoint difference estimation model M3.

Example 6-2

Figure 36:
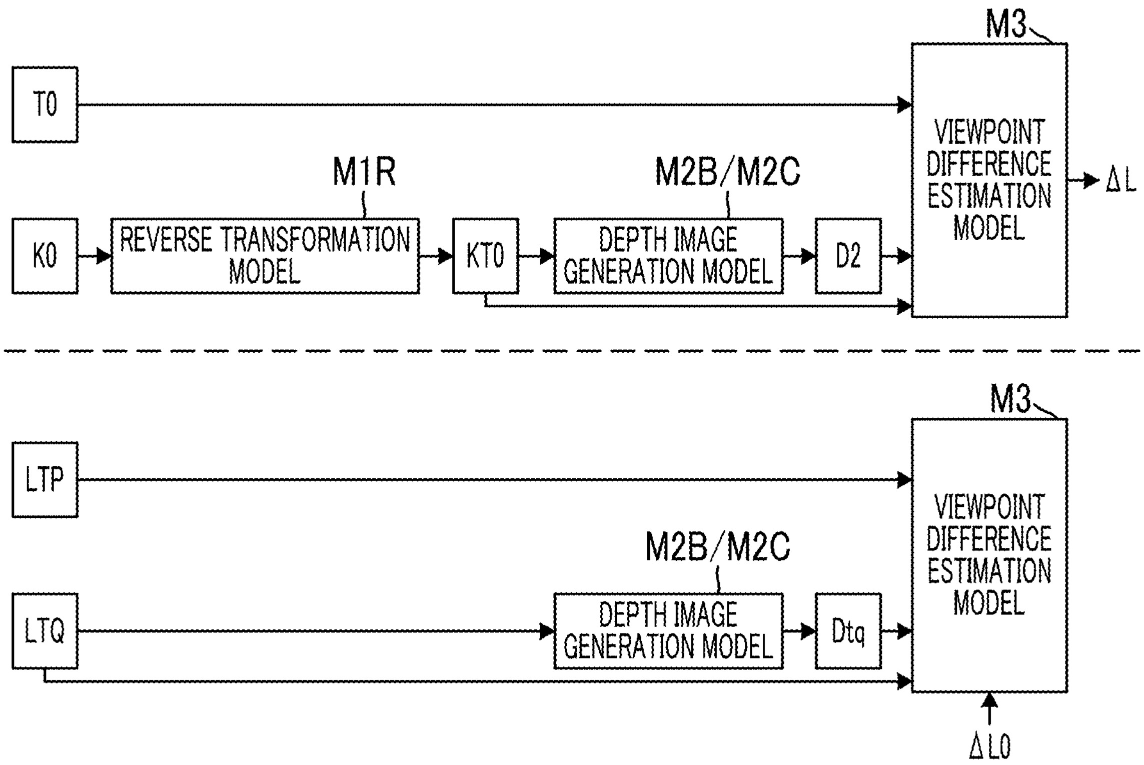
FIG. 36 is a diagram showing contents of viewpoint difference estimation processing according to Example 6-2.

FIG. 36 shows an overview of viewpoint difference estimation processing according to Example 6-2. In the training phase in the present example, the training unit 15 generates the depth image Dtq by inputting the real image for training LTQ to the depth image generation model M2B or M2C. In addition, the training unit 15 trains the viewpoint difference estimation model M3 by using, as training data, the viewpoint difference ΔL0 between the real images for training LTP and LKQ, the depth images Dq, and the real images for training LTP and LTQ.

In the operational phase in the present example, the transformation unit 12 transforms the virtual image K0 into the virtual-to-real transformed image KT0 by inputting the virtual image K0 to the reverse transformation model M1R. In addition, the generation unit 13 generates the second depth image D2 by inputting the virtual-to-real transformed image KT0 to the depth image generation model M2B or M2C. The estimation unit 14 estimates the viewpoint difference ΔL by inputting the second depth image D2, the real image T0, and the virtual-to-real transformed image KT0 to the viewpoint difference estimation model M3.

As described above with reference to Examples, the viewpoint difference estimation model M3 according to the present embodiment may be a model that has been trained through supervised learning using training data including a combination of at least one of the real image for training, which is captured by the endoscope inserted into the tubular structure of the subject and which represents the interior wall of the tubular structure, or the depth image for training, which represents the distance for each pixel from the viewpoint of the real image for training to the interior wall of the tubular structure, at least one of the virtual image for training, which is generated based on the three-dimensional image V0 of the subject and which represents, in a pseudo manner, the interior wall of the tubular structure as viewed from the virtual viewpoint P3 predetermined in the three-dimensional image, or the virtual depth image for training, which represents the distance for each pixel from the virtual viewpoint P3 to the interior wall of the tubular structure, and the viewpoint difference ΔL0 between the viewpoint of the real image for training and the virtual viewpoint P3. The virtual viewpoint P3 is an example of a third viewpoint according to the present disclosure.

It should be noted that, in the embodiment described above, the form has been described in which the second depth image D2 based on the virtual image K0 used to estimate the viewpoint difference ΔL is generated by using the depth image generation model M2 based on the pixel value of the virtual image K0, but the present disclosure is not limited to this. The second depth image based on the virtual image K0 may be generated based on the distance information from the virtual viewpoint P10 in the three-dimensional image V0 to the interior wall of the tubular structure. With such a form, it is possible to obtain a more accurate second depth image D2 including accurate scale information. In this case, the generation of the virtual image K0 by the acquisition unit 11 may be omitted.

Here, the distance information indicates, for example, a distance from the virtual viewpoint P10 in the three-dimensional image V0 to a point at which the opacity is equal to or greater than the predetermined value. In a case in which the opacity is equal to or greater than the predetermined value in the three-dimensional image V0, it is considered that the portion corresponds to the interior wall of the tubular structure. In addition, for example, in a case in which the bronchus image B0 is generated based on the three-dimensional image V0, the distance information may indicate a distance from the virtual viewpoint P10 to a surface of the bronchus image B0.

Figure 37:
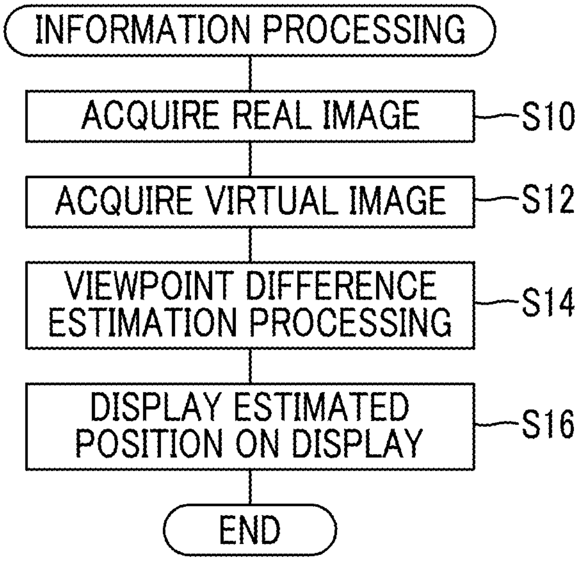
FIG. 37 is a flowchart showing an example of information processing.

Next, description of actions of the information processing apparatus 10 according to the present embodiment will be made with reference to FIG. 37. In the information processing apparatus 10, in a case in which the CPU 21 executes the information processing program 27, information processing shown in FIG. 37 is executed. The information processing is executed, for example, in a case in which the user gives an instruction to start the execution. It should be noted that the information processing shown in FIG. 37 corresponds to the form example described with reference to FIG. 6, and various modifications described above can be made.

In step S10, the acquisition unit 11 acquires the real image T0 captured by the endoscope 31 disposed at the predetermined viewpoint position in the bronchus. In Step S12, the acquisition unit 11 acquires the virtual image K0 which is generated based on the three-dimensional image of the subject and which represents, in a pseudo manner, the interior wall of the tubular structure as viewed from the virtual viewpoint P10 predetermined in the three-dimensional image.

In step S14, the transformation unit 12, the generation unit 13, and the estimation unit 14 perform the viewpoint difference estimation processing of estimating the viewpoint difference ΔL between the viewpoint P11 of the real image T0 acquired in step S10 and the virtual viewpoint P10. In step S16, the controller 16 performs control of displaying the estimated position Pt of the endoscope distal end 3B estimated based on the viewpoint difference ΔL estimated in step S14 on the display 24, and terminates the present information processing.

Figure 38:
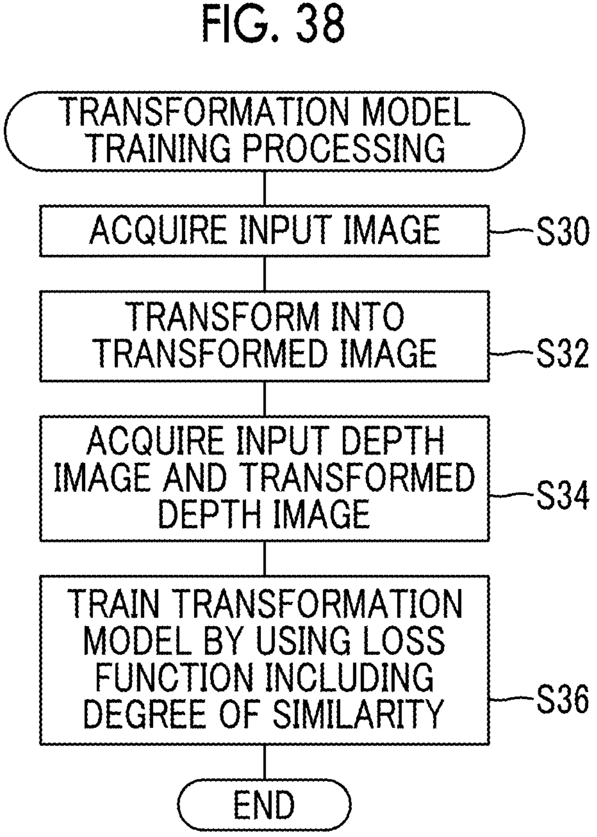
FIG. 38 is a flowchart showing an example of transformation model training processing.

Next, description of the training processing of the transformation model M1 by the training unit 15 according to the present embodiment will be made with reference to FIG. 38. In the information processing apparatus 10, in a case in which the CPU 21 executes the information processing program 27, transformation model training processing shown in FIG. 38 is executed. The transformation model training processing is executed, for example, in a case in which the user gives an instruction to start the execution. It should be noted that the transformation model training processing shown in FIG. 38 corresponds to the form example described using FIG. 11, and various modifications described above can be made.

In step S30, the training unit 15 acquires the input image including any one of the real image T0, which is captured by the endoscope and which represents the interior wall of the tubular structure, or a virtual image K0, which is generated based on the three-dimensional image V0 of the subject and which represents, in a pseudo manner, the interior wall of the tubular structure as viewed from the virtual viewpoint P10 predetermined in the three-dimensional image V0. In step S32, the training unit 15 transforms the input image acquired in step S30 into the transformed image that is an image style that is not included in the input image.

In step S34, the training unit 15 acquires the depth image (input depth image) of the input image acquired in step S30 and the depth image (transformed depth image) of the transformed image transformed in step S32, by using the depth image generation model M2. In step S36, the training unit 15 trains the transformation model M1 by using the loss function including the degree of similarity between the input depth image and the transformed depth image acquired in step S34. In a case in which step S36 is completed, the transformation model training processing is terminated.

As described above, one aspect of the present disclosure relates to the information processing apparatus 10 comprising: at least one processor, in which the processor uses at least one of the real image, which is captured by the endoscope inserted into the tubular structure of the subject and which represents the interior wall of the tubular structure, or the first depth image, which represents the distance for each pixel from the viewpoint of the real image to the interior wall of the tubular structure, and at least one of the virtual image, which is generated based on the three-dimensional image of the subject and which represents, in a pseudo manner, the interior wall of the tubular structure as viewed from the virtual viewpoint predetermined in the three-dimensional image, or the second depth image, which represents the distance for each pixel from the virtual viewpoint to the interior wall of the tubular structure, to perform the viewpoint difference estimation processing of estimating the viewpoint difference between the viewpoint of the real image and the virtual viewpoint, and uses at least one of the first depth image or the second depth image in the viewpoint difference estimation processing.

That is, with the information processing apparatus 10 according to one aspect of the present disclosure, the viewpoint difference ΔL between the viewpoint P11 of the real image T0 and the virtual viewpoint P10 is estimated by using at least any of the first depth image D1 or the second depth image D2. Therefore, the viewpoint difference ΔL between the viewpoint P11 of the real image T0 of the endoscope and the virtual viewpoint P10 that is virtually set can be accurately estimated.

In addition, one aspect of the present disclosure relates to the information processing apparatus 10 comprising: at least one processor, in which the processor acquires the input image including any one of the real image, which is captured by the endoscope inserted into the tubular structure of the subject and which represents the interior wall of the tubular structure, or the virtual image, which is generated based on the three-dimensional image of the subject and which represents, in a pseudo manner, the interior wall of the tubular structure as viewed from the virtual viewpoint predetermined in the three-dimensional image, uses the transformation model, which is trained to transform any one of the input real image or virtual image into the image style of the other of the input real image or virtual image, to transform the input image into the transformed image having the image style that is not included in the input image, acquires the input depth image, which represents the distance for each pixel from the viewpoint of the input image to the interior wall of the tubular structure, and the transformed depth image, which represents the distance for each pixel from the viewpoint of the transformed image to the interior wall of the tubular structure, and trains the transformation model by using the loss function including the degree of similarity between the input depth image and the transformed depth image.

That is, with the information processing apparatus 10 according to one aspect of the present disclosure, for example, it is possible to apply, to the transformation model M1 that transforms the real image T0 into the transformed image having the virtual image style, a constraint so that the depth image does not change before and after the transformation. Therefore, it is possible to prevent the bronchus structure and the like included in the image from changing before and after transformation and to obtain a highly accurate transformed image. As a result, since the highly accurate transformed image can be input to the machine learning model used in the endoscope navigation, such as the depth image generation model M2 and the viewpoint difference estimation model M3, which are trained by using the transformed image, it is possible to contribute to the effect of accurately estimating the viewpoint difference ΔL between the viewpoint P11 of the real image T0 of the endoscope and the virtual viewpoint P10 that is virtually set.

In addition, in each embodiment, for example, as hardware structures of processing units that execute various types of processing, such as the acquisition unit 11, the transformation unit 12, the generation unit 13, the estimation unit 14, the training unit 15, and the controller 16, various processors shown below can be used. As described above, in addition to the CPU that is a general-purpose processor that executes software (program) to function as various processing units, the various processors include a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by using one of the various processors or may be configured by using a combination of two or more processors of the same type or different types (for example, a combination of a plurality of FPGAs or a combination of a CPU and an FPGA). In addition, a plurality of the processing units may be configured by one processor.

A first example of the configuration in which the plurality of processing units are configured by using one processor is a form in which one processor is configured by using a combination of one or more CPUs and the software and this processor functions as the plurality of processing units, as represented by computers, such as a client and a server. Second, as represented by a system on chip (SoC) or the like, there is a form in which the processor is used in which the functions of the entire system which includes the plurality of processing units are realized by a single integrated circuit (IC) chip. In this way, as the hardware structure, the various processing units are configured by using one or more of the various processors described above.

Further, the hardware structure of these various processors is, more specifically, an electric circuit (circuitry) in which circuit elements such as semiconductor elements are combined.

In addition, in the embodiment described above, an aspect has been described in which the information processing program 27 of the information processing apparatus 10 is stored in the storage unit 22 in advance, but the present disclosure is not limited to this. The information processing program 27 may be provided in a form of being recorded in a recording medium, such as a compact disc read only memory (CD-ROM), a digital versatile disc read only memory (DVD-ROM), and a universal serial bus (USB) memory. In addition, a form may be adopted in which the information processing program 27 is downloaded from an external apparatus via the network. Further, the technique of the present disclosure extends to a storage medium that non-transitorily stores a program in addition to the program.

In the technique of the present disclosure, the embodiments and the examples described above can be combined as appropriate. The above-described contents and the above-shown contents are detailed description for parts according to the technique of the present disclosure, and are merely examples of the technique of the present disclosure. For example, the above description related to the configuration, the function, the action, and the effect is the description related to the examples of the configuration, the function, the action, and the effect of the parts according to the technique of the present disclosure. As a result, it is needless to say that unnecessary parts may be deleted, new elements may be added, or replacements may be made with respect to the above-described contents and the above-shown contents within a range that does not deviate from the gist of the technique of the present disclosure.

Regarding the embodiment described above, the following supplementary notes are further disclosed.

Supplementary Note 1

An information processing apparatus comprising: at least one processor, in which the processor acquires an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image, uses a transformation model, which is trained to transform any one of the input real image or virtual image into an image style of the other of the input real image or virtual image, to transform the input image into a transformed image having an image style that is not included in the input image, acquires an input depth image, which represents a distance for each pixel from a viewpoint of the input image to the interior wall of the tubular structure, and a transformed depth image, which represents a distance for each pixel from a viewpoint of the transformed image to the interior wall of the tubular structure, and trains the transformation model by using a loss function including a degree of similarity between the input depth image and the transformed depth image.

Supplementary Note 2

The information processing apparatus according to supplementary note 1, in which the transformation model is obtained by a generative adversarial network that has been trained by using training data including a real image for training, which is captured by the endoscope inserted into the tubular structure of the subject and which represents the interior wall of the tubular structure, and a virtual image for training, which is generated based on a three-dimensional image of a subject that is the same as or different from the subject of the real image for training and which represents, in a pseudo manner, the interior wall of the tubular structure as viewed from the virtual viewpoint predetermined in the three-dimensional image.

Supplementary Note 3

The information processing apparatus according to supplementary note 1 or 2, in which the input image includes the real image, the transformation model is a learning model trained to receive input of the real image, transform the input real image into a virtual image style, and output the transformed real image, and the processor transforms the real image into a transformed image having the virtual image style by using the transformation model.

Supplementary Note 4

The information processing apparatus according to supplementary note 1 or 2, in which the input image includes the virtual image, the transformation model is a learning model trained to receive input of the virtual image, transform the input virtual image into a real image style, and output the transformed virtual image, and the processor transforms the virtual image into a transformed image having the real image style by using the transformation model.

Supplementary Note 5

The information processing apparatus according to any one of supplementary notes 1 to 4, in which the processor uses a depth image generation model that has been trained in advance to receive input of an image, which represents the interior wall of the tubular structure, and output a depth image, which represents a distance for each pixel from the viewpoint of the input image to the interior wall of the tubular structure, to generate the input depth image based on the input image and the transformed depth image based on the transformed image.

Supplementary Note 6

The information processing apparatus according to supplementary note 5, in which the depth image generation model is a model that has been trained in advance through supervised learning using training data including a combination of a virtual image for training, which is generated based on the three-dimensional image of the subject and which represents, in a pseudo manner, the interior wall of the tubular structure as viewed from the virtual viewpoint predetermined in the three-dimensional image, and a depth image for training, which is generated based on distance information from the virtual viewpoint in the three-dimensional image to the interior wall of the tubular structure and which represents a distance for each pixel from the virtual viewpoint to the interior wall of the tubular structure.

Supplementary Note 7

The information processing apparatus according to supplementary note 5, in which the depth image generation model is a model that has been trained in advance through supervised learning using training data including a combination of an image obtained by transforming a virtual image for training, which is generated based on the three-dimensional image of the subject and which represents, in a pseudo manner, the interior wall of the tubular structure as viewed from the virtual viewpoint predetermined in the three-dimensional image, into a real image style by using a transformation model that has been trained in advance to receive input of the virtual image, transform the input virtual image into the real image style, and output the transformed virtual image, and a depth image for training, which is generated based on distance information from the virtual viewpoint in the three-dimensional image to the interior wall of the tubular structure and which represents a distance for each pixel from the virtual viewpoint to the interior wall of the tubular structure.

Supplementary Note 8

The information processing apparatus according to supplementary note 5, in which the depth image generation model is a model that has been trained through supervised learning using training data including a combination of a real image for training, which is captured by the endoscope inserted into the tubular structure of the subject and which represents the interior wall of the tubular structure, and a depth image for training, which is generated based on distance information from a viewpoint corresponding to a viewpoint at which the real image for training is captured, in the three-dimensional image of the subject, to the interior wall of the tubular structure and which represents a distance for each pixel from the viewpoint corresponding to the viewpoint at which the real image for training is captured to the interior wall of the tubular structure.

Supplementary Note 9

The information processing apparatus according to supplementary note 5, in which the depth image generation model is a model that has been trained in advance through supervised learning using training data including a combination of a real image for training, which is captured by the endoscope inserted into the tubular structure of the subject and which represents the interior wall of the tubular structure, and a depth image for training, which is generated based on an actual measurement value of a distance from a viewpoint at which the real image for training is captured to the interior wall of the tubular structure, the actual measurement value being obtained by a distance-measuring sensor mounted on the endoscope, and which represents a distance for each pixel from the viewpoint at which the real image for training is captured to the interior wall of the tubular structure.

Supplementary Note 10

An information processing method including: acquiring an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image; using a transformation model, which is trained to transform any one of the input real image or virtual image into an image style of the other of the input real image or virtual image, to transform the input image into a transformed image having an image style that is not included in the input image; acquiring an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and training the transformation model by using a loss function including a degree of similarity between the input depth image and the transformed depth image.

Supplementary Note 11

An information processing program for causing a computer to execute a process including: acquiring an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image; using a transformation model, which is trained to transform any one of the input real image or virtual image into an image style of the other of the input real image or virtual image, to transform the input image into a transformed image having an image style that is not included in the input image; acquiring an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and training the transformation model by using a loss function including a degree of similarity between the input depth image and the transformed depth image.

What is claimed is:

1. An information processing apparatus comprising at least one processor, wherein the processor is configured to:

acquire an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image;

use a transformation model, which is trained to transform any one of the input real image or virtual image into an image style of the other of the input real image or virtual image, to transform the input image into a transformed image having an image style that is not included in the input image;

acquire an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and train the transformation model by using a loss function including a degree of similarity between the input depth image and the transformed depth image.

2. The information processing apparatus according to claim 1, wherein the transformation model is obtained by a generative adversarial network that has been trained by using training data including:

a real image for training, which is captured by the endoscope inserted into the tubular structure of the subject and which represents the interior wall of the tubular structure; and a virtual image for training, which is generated based on a three-dimensional image of a subject that is the same as or different from the subject of the real image for training and which represents, in a pseudo manner, the interior wall of the tubular structure as viewed from the virtual viewpoint predetermined in the three-dimensional image.

3. The information processing apparatus according to claim 1, wherein:

the input image includes the real image, the transformation model is a learning model trained to receive input of the real image, transform the input real image into a virtual image style, and output the transformed real image, and the processor is configured to transform the real image into a transformed image having the virtual image style by using the transformation model.

4. The information processing apparatus according to claim 1, wherein:

the input image includes the virtual image, the transformation model is a learning model trained to receive input of the virtual image, transform the input virtual image into a real image style, and output the transformed virtual image, and the processor is configured to transform the virtual image into a transformed image having the real image style by using the transformation model.

5. The information processing apparatus according to claim 1, wherein the processor is configured to use a depth image generation model that has been trained in advance to receive input of an image, which represents the interior wall of the tubular structure, and output a depth image, which represents a distance for each pixel from the viewpoint of the input image to the interior wall of the tubular structure, to generate the input depth image based on the input image and the transformed depth image based on the transformed image.

6. The information processing apparatus according to claim 5, wherein the depth image generation model is a model that has been trained in advance through supervised learning using training data including a combination of:

a virtual image for training, which is generated based on the three-dimensional image of the subject and which represents, in a pseudo manner, the interior wall of the tubular structure as viewed from the virtual viewpoint predetermined in the three-dimensional image; and a depth image for training, which is generated based on distance information from the virtual viewpoint in the three-dimensional image to the interior wall of the tubular structure and which represents a distance for each pixel from the virtual viewpoint to the interior wall of the tubular structure.

7. The information processing apparatus according to claim 5, wherein the depth image generation model is a model that has been trained in advance through supervised learning using training data including a combination of:

an image obtained by transforming a virtual image for training, which is generated based on the three-dimensional image of the subject and which represents, in a pseudo manner, the interior wall of the tubular structure as viewed from the virtual viewpoint predetermined in the three-dimensional image, into a real image style by using a transformation model that has been trained in advance to receive input of the virtual image, transform the input virtual image into the real image style, and output the transformed virtual image; and a depth image for training, which is generated based on distance information from the virtual viewpoint in the three-dimensional image to the interior wall of the tubular structure and which represents a distance for each pixel from the virtual viewpoint to the interior wall of the tubular structure.

8. The information processing apparatus according to claim 5, wherein the depth image generation model is a model that has been trained through supervised learning using training data including a combination of:

a real image for training, which is captured by the endoscope inserted into the tubular structure of the subject and which represents the interior wall of the tubular structure; and a depth image for training, which is generated based on distance information from a viewpoint corresponding to a viewpoint at which the real image for training is captured, in the three-dimensional image of the subject, to the interior wall of the tubular structure and which represents a distance for each pixel from the viewpoint corresponding to the viewpoint at which the real image for training is captured to the interior wall of the tubular structure.

9. The information processing apparatus according to claim 5, wherein the depth image generation model is a model that has been trained in advance through supervised learning using training data including a combination of:

a real image for training, which is captured by the endoscope inserted into the tubular structure of the subject and which represents the interior wall of the tubular structure; and a depth image for training, which is generated based on an actual measurement value of a distance from a viewpoint at which the real image for training is captured to the interior wall of the tubular structure, the actual measurement value being obtained by a distance-measuring sensor mounted on the endoscope, and which represents a distance for each pixel from the viewpoint at which the real image for training is captured to the interior wall of the tubular structure.

10. An information processing method comprising:

acquiring an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image;

using a transformation model, which is trained to transform any one of the input real image or virtual image into an image style of the other of the input real image or virtual image, to transform the input image into a transformed image having an image style that is not included in the input image;

acquiring an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and training the transformation model by using a loss function including a degree of similarity between the input depth image and the transformed depth image.

11. A non-transitory computer-readable storage medium storing an information processing program for causing a computer to execute a process comprising:

acquiring an input image including any one of a real image, which is captured by an endoscope inserted into a tubular structure of a subject and which represents an interior wall of the tubular structure, or a virtual image, which is generated based on a three-dimensional image of the subject and which represents, in a pseudo manner, the interior wall of the tubular structure as viewed from a virtual viewpoint predetermined in the three-dimensional image;

using a transformation model, which is trained to transform any one of the input real image or virtual image into an image style of the other of the input real image or virtual image, to transform the input image into a transformed image having an image style that is not included in the input image;

acquiring an input depth image, which represents a distance for each pixel from a viewpoint of the input image to the interior wall of the tubular structure, and a transformed depth image, which represents a distance for each pixel from a viewpoint of the transformed image to the interior wall of the tubular structure; and training the transformation model by using a loss function including a degree of similarity between the input depth image and the transformed depth image.

* * * * *